(12) United States Patent
Esuvaranathan et al.

(10) Patent No.: US 7,709,457 B2
(45) Date of Patent: *May 4, 2010

(54) METHODS AND COMPOSITIONS FOR DELIVERY OF PHARMACEUTICAL AGENTS

(75) Inventors: Kesavan Esuvaranathan, Singapore (SG); Ratha Mahendran, Singapore (SG); Carmel Lawrencia, Singapore (SG)

(73) Assignee: Genecure Pte Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 11/986,829

(22) Filed: Nov. 26, 2007

(65) Prior Publication Data

US 2009/0054364 A1 Feb. 26, 2009

Related U.S. Application Data

(63) Continuation of application No. 10/086,973, filed on Mar. 1, 2002, now Pat. No. 7,320,963.

(30) Foreign Application Priority Data

Sep. 1, 1999 (AU) .................................. PQ2593
Sep. 1, 2000 (WO) ..................... PCT/SG00/00130

(51) Int. Cl.
A61K 31/715 (2006.01)
G01N 31/00 (2006.01)
G01N 33/00 (2006.01)

(52) U.S. Cl. .......................... 514/44; 424/93.2; 514/58; 436/15; 436/71

(58) Field of Classification Search ........................ None
See application file for complete search history.

(56) References Cited

U.S. PATENT DOCUMENTS

| 5,264,618 | A | 11/1993 | Felgner et al. |
| 5,580,859 | A | 12/1996 | Felgner et al. |
| 5,605,890 | A | 2/1997 | Agrawal et al. |
| 5,614,503 | A | 3/1997 | Chaudhary et al. |
| 5,691,316 | A | 11/1997 | Agrawal et al. |
| 7,320,963 | B2 * | 1/2008 | Esuvaranathan et al. ...... 514/44 |
| 2003/0166601 | A1 | 9/2003 | Woodle et al. |

FOREIGN PATENT DOCUMENTS

| CA | 2161225 | A | 10/1994 |
| CA | 2193502 | A | 12/1995 |
| CA | 2199004 | A | 3/1996 |
| CA | 2263705 | A | 2/1998 |
| CA | 2303884 | A1 | 4/1999 |
| WO | WO-94/23697 | A1 | 10/1994 |
| WO | WO-96/08235 | A1 | 3/1996 |
| WO | WO-96/37194 | A1 | 11/1996 |
| WO | WO-96/40962 | A1 | 12/1996 |
| WO | WO-96/40963 | A1 | 12/1996 |
| WO | WO-98/07408 | A1 | 2/1998 |
| WO | WO-98/13026 | A1 | 4/1998 |
| WO | WO-98/40499 | A1 | 9/1998 |
| WO | WO-98/44909 | A1 | 10/1998 |
| WO | WO-98/51285 | A2 | 11/1998 |
| WO | WO-98/51285 | A3 | 11/1998 |
| WO | WO-99/15206 | A1 | 4/1999 |

OTHER PUBLICATIONS

Sutton (Mol. Ther. 2(3): 211-217, 2000).*
Cardillo et al (Anticancer Res. 20(6B): 4579-4583, 2000).*
Medline Accession No. 2004528586 (2004).*
Syrigos et al (Urology 61(3): 677-680, 2003).*
Grignon et al (Cancer Res. 56(7): 1654-1659, 1996).*
Medline Accession No. 2002430653.*
A Conference Supplement to Cancer Gene Therapy. ( Nov./Dec. 1999) Gene Therapy of Cancer VIII. San Diego, California Dec. 9-11, 1999. 6(6): two pages.
Abdou, S. et al. (1997). "Beta-Cyclodextrin Derivatives as Carriers to Enhance the Antivural Activity of an Antisense Oligonucleotide Directed Toward A Coronavirus Intergenic Consensus Sequence," Arch. Virol. 142:1585-1602.
Abe, K. et al. (1995). "Enhanced Nasal Delivery of Luteinizing Hormone Releasing Hormone Agonist Buserelin by Oleic Acid Solubilized and Stabilized in Hydroxypropyl-β-Cyclodextrin," Chem. Pharm. Bull. 43(12):2232-2237.
Alton, E.W. et al. (Oct. 1993). "Non-Invasive Liposome-Mediated Gene Delivery Can Correct the Ion Transport Defect in Cystic Fibrosis Mutant Mice," Natl. Genet. 5:135-142.
Becket, G. et al. (1999). "Improvement of the In Vitro Dissolution of Praziquantal by Complexation with ?-β- and ?-Cyclodextrins," Int. J. Pharm. 179:65-71.
Belldegrun, A.S. et al. ( Jun. 1998). "Superficial Bladder Cancer: The Role of Interferon-," The J. of Urology 159:1793-1801.
Bennett, M.J. et al. (Feb. 1995). "Cholesterol Enhances Cationic Liposome-Mediated DNA Transfection of Human Respiratory Epithelial Cells," Biosci. Rep. 15(1):47-53.
Bibby, D.C. et al. (2000). Mechanisms by Which Cyclodextrins Modify Drug Release from Polymeric Drug Delivery Systems, Int. J. Pharm. 197:1-11.

(Continued)

Primary Examiner—Richard Schnizer
(74) Attorney, Agent, or Firm—Morrison & Foerster LLP

(57) ABSTRACT

Methods and compositions for delivering pharmaceutical agents into cells, in particular urothelial cells of the bladder, are provided. In the methods and compositions of the invention, a solubilized cholesterol composition is used to facilitate delivery of pharmaceutical agents. Preferably, the cholesterol is solubilized by a cyclodextrin (e.g., methyl-β-cyclodextrin) and the pharmaceutical agent comprises a polynucleotide and either a cationic lipid, a cationic polymer or a dendrimer. Improved methods for transfecting polynucleotides into cells thus are also provided, using cationic lipids, cationic polymers or dendrimers and solubilized cholesterol, wherein the transfection efficiency is enhanced compared to use of cationic lipids, cationic polymers or dendrimers alone. Preferred methods of the invention involve transfecting polynucleotides into urothelial cells, preferably for therapeutic treatment of bladder cancer using, for example, a polynucleotide (s) encoding an interleukin(s), an interferon(s), a colony stimulating factor(s) and/or a tumor suppressor(s).

14 Claims, 15 Drawing Sheets

OTHER PUBLICATIONS

Brand, K. (2002). "Cancer Gene Therapy With Tissue Inhibitors of Metalloproteinases (TIMPs)," Current Gene Therapy 2(2):255-271.

Brigham, K.L. MD et al. (Oct. 1989). "Rapid Communication: In Vivo Transfection of Murine Lungs with a Functioning Prokaryotic Gene Using a Liposome Vehicle," Am. J. Med. Sci. 298(4):278-281.

Brosman, S.A. (Aug. 1992). "Bacillus Calmette-Guérin Immunotherapy," Urol. Clin. of North Am. 19(3):557-564.

Bui, L.A. (Dec. 1997). "In Vivo Therapy of Hepatocellular Carcinoma with a Tumor-Specific Adenoviral Vector Expressing Interleukin-2," Hum. Gene Ther. 8:2173-2182.

Cardillo, M.R. (2000). "Heat Shock Protein-90, IL-6 and IL-10 in Bladder Cancer," Anticancer Res. 20(6B):4579-4583.

Chang, S.-L. et al. (1998). "Transdermal Iontophoretic Delivery of Hydrocortisone from Cyclodextrin Solutions," J. Pharm. Pharmacol. 50:635-640.

Chen, L. (1997). "Eradication of Murine Bladder Carcinoma by Intratumor Injection of a Bicistronic Adenoviral Vector Carrying cDNAs for the IL-12 Heterodimer and its Inhibition by the IL-12 p40 Subunit Homodimer," J. Immunology 159:351-359.

Chow, N.-H. et al. (1998). "Potential Value of Urinary Intercellular Adhesion Molecule-1 Determination in Patients with Bladder Cancer," Adult Urol. 52(6):1015-1019.

Colombo, M.P. et al. (Feb. 1994). "Cytokine Gene Transfer in Tumor Inhibition and Tumor Therapy: Where Are We Now?" Imm. Today 15(2):48-51.

Crook, K. et al. (1998). "Inclusion of Cholesterol in DOTAP Transfection Complexes Increases the Delivery of DNA to Cells In Vitro in the Presence of Serum," Gene Ther. 5:137-143.

Cross, A.H. et al. (2000). "A Catalyst of Peroxynitrite Decompositon Inhibits Murine Experimental Autoimmune Encephalomyelitis," J. of Neuro. 107:21-28.

Croyle, M.A. et al. (1998). "Beta Cyclodextrins Enhance Adenoviral-Mediated Gene Delivery to the Intestine," Pharm. Res. 15(9):1348-1355.

Debs, R.J. et al. (Jun. 1990). "Regulation of Gene Expression In Vivo by Liposome-mediated Delivery of a Purified Transcription Factor," J. Biol. Chem. 265(18):10189-10192.

Eastman, S.J. et al. (Apr. 1997). "A Concentrated and Stable Aerosol Formulation of Cationic Lipid: DNA Complexes Giving High-level Gene Expression in Mouse Lung," Hum. Gene. Ther. 8(6):765-773.

Felgner, J.H. et al. (Jan. 1994). "Enhanced Gene Delivery and Mechanism Studies with a Novel Series of Cationic Lipid Formulations," J. Biol. Chem. 269(4):2550-2561.

Felgner, P.L. et al. (Nov. 1987). "Lipofection: A Highly Efficient, Lipid-mediated DNA-Transfection Procedure," Proc. Natl. Acad. Sci. U.S.A. 84:7413-7416.

Freeman, D.J. and Niven, R. W. (1996). "The Influence of Sodium Glycocholate and other Additives on the In Vivo Transfection of Plasmid DNA in the Lungs," Pharm. Res. 13(2):202-209.

Gabrilovich, D.I. et al. (1996). "Dendritic Cells in Antitumor Immune Responses. I. Defective Antigen Presentation in Tumor-Bearing Hosts," Cell. Imm. 170(139):101-110.

Gan, Y.H. et al. (1999). "Antitumour Immunity of Bacillus Calmette-Guerin and Interferon Alpha in Murine Bladder Cancer," Eur. J. Cancer 35(7):1123-1129.

Gao, X. et al. (Jan. 1996). "Potentiation of Cationic Liposome-Mediated Gene Delivery by Polycations," Biochem. 35(3):1027-1036.

Gimpl, G. et al. (1997). "Cholesterol as Modulator of Receptor Function," Biochem. 36(36):10959-10974.

Goeddel, D.V. ed. (1990). Methods in Enzymology:Gene Expression Technology, Academic Press Inc.: San Diego, CA, 185:v-ix, (Table of Contents Only.).

Golumbek, P.T. et al. (Nov. 1991). "Treatment of Established Renal Cancer by Tumor Cells Engineered to Secrete Interlukin-4," Science 254(5032):713-716.

Gonzalez, H. et al. (1999). "New Class of Polymers for the Delivery of Macromolecular Therapeutics," Bioconj. Chem. 10:1068-1074.

Grignon, D.J. et al. (Apr. 1, 1996). "High Levels of Tissue Inhibitor of Metalloproteinase-2 (TIMP-2) Expression Are Associated with Poor Outcome in Invasive Bladder Cancer," Cancer Res. 56:1654-1659.

Grosse, P.Y. et al. (1998). "Antiproliferative Effect of Methyl-?-Cyclodextrin In Vitro and in Human Tumour Xenografted Athymic Nude Mice," Br. J. of Can. 78(9):1165-1169.

Harimoto, K. et al. (1998). "In Vivo Gene Transfer Methods in the Bladder Without Viral Vectors," Br. J. of Urol. 81:870-874.

Hofland, H.E. (Jul. 1996). "Formation of Stable Cationic Lipid/DNA Complexes for Gene Transfer," Proc. Nat. Acad Sci U.S.A. 93(14):7305-7309.

Hovgaard, L. et al. (1995). "Drug Delivery Studies in Caco-2 Monolayers. IV. Absorption Enhancer Effects of Cyclodextrins," Pharm. Res. 12(9):1328-1332.

Hui, S.W. et al. (Aug. 1996). "The Role of Helper Lipids in Cationic Liposome-mediated Gene Transfer," Biophys J. 71:590-599.

Hyde, S.C. et al. (Mar. 1993). "Correction of the Ion Transport Defect in Cystic Fibrosis Transgenic Mice by Gene Therapy," Nature 362(6417):250-255.

Jackson, A.M. et al. (1995). "Changes in Urinary Cytokines and Soluble Intercellular Adhesion Molecule-1 (ICAM-1) in Bladder Cancer Patients After Bacillus Calmette-Guérin (BCG) Immunotherapy," Clin. Exp. Immunol. 99:369-375.

Kaufman, R.J. et al. (Jan. 1987). "Translational Efficiency of Polycistronic mRNAs and Their Utilization to Express Heterologous Genes in Mammalian Cells," EMBO J. 6:187-193.

Kurisu, H. et al. (1994). "Cytokine-mediated Antitumor Effect of Bacillus Calmette-Guérin on Tumor Cells In Vitro," Cancer Immunol. Immunother. 39:249-253.

Lamm, D.L., MD (Aug. 1992). "Complications of Bacillus Calmette-Guérin Immunotherapy," Urol. Clin. North Am. 19(3):565-572.

Lasic, D.D. et al. (1996). "Liposomes in Gene Therapy," Adv. Drug Deliv. Rev. 20:221-266.

Lawrencia, C. et al. (Dec. 1999). Conference Supplement to Cancer Gene Therapy VII.

Lawrencia, C. et al. (2001). "Transfection of Urothelial Cells Using Methyl-?-Cyclodextrin Solubilized Cholesterol and Dotap," Gene Therapy 8:760-768.

Lee, E.R. et al. (Sep. 1996). "Detailed Analysis of Structures and Formulations of Cationic Lipids for Efficient Gene Transfer to the Lung," Hum. Gene Ther. 7(14):1701-1717.

Lee, S.S. et al. (Jul. 1994). "Intravesical Gene Therapy: In Vivo Gene Transfer Using Recombinant Vaccinia Virus Vectors," Cancer Res. 54:3325-3328.

Li, Y. et al. (Jan. 1999). "Loss of Adenoviral Receptor Expression in Human Bladder Cancer Cells: A Potential Impact on the Efficacy of Gene Therapy," Cancer Res. 59:325-330.

Liu, F. et al. (1996). "Effect of Non-Ionic Surfactants on the Formation of DNA/Emulsion Complexes and Emulsion-Mediated Gene Transfer," Pharm. Res. 13(11):1642-1646.

Liu, F. et al. (Dec. 1996). "New Cationic Lipid Formulations for Gene Transfer," Pharma. Res. 13(12):1856-1860.

Loftsson, T. (1998). "Increasing the Cyclodextrin Complexation of Drugs and Drug Biovailability Through Addition of Water-Soluble Polymers," Pharmazie 53(11):733-740.

Lopez, R.F.V. et al. (2000). "Influence of Cyclodextrin Complexation on the In Vitro Permeation and Skin Metabolism of Dexamethasone," Int. J. Pharm, 200:127-132.

Malone, R.W. et al. (Aug. 1989). "Cationic Liposome-mediated RNA Transfection," Proc. Natl. Acad. Sci. U.S.A. 86:6077-6081.

Medline Accession No. 2002430653, created on Aug. 21, 2002, last updated on Oct. 29, 2002, one page.

Medline Accession No. 2004528586, created on Oct. 23, 2004, last updated on Feb. 11, 2005, one page.

Milelia, M. (1999). "Interleukin-2 Gene Transfer Into Human Transitional Cell Carcinoma of the Urinary Bladder," Brit. J. of Can. 79(5/6):770-779.

Mizoguchi, H. et al. (Dec. 1992). "Alterations in Signal Transduction Molecules in T Lymphocytes from Tumor-Bearing Mice," Science 258:1795-1798.

Morales, A. et al. (Aug. 1976). "Intracavitary Bacillus Calmette-Guerin in the Treatment of Superficial Bladder Tumors," J. Urol. 116:180-183.

Morris, B.D. et al. (Aug. 1994). "Adenoviral-mediated Gene Transfer to Bladder In Vivo," J. Urol. 152:506-509.

Nabel, E.G. et al. (Jun. 1992). "Transduction of a Foreign Histocompatibility Gene into the Arterial Wall Induces Vasculitis," Proc. Nat. Acad. Sci. U.S.A. 89(11):5157-5161.

Nabel, E.G. et al. (Sep. 1990). "Site-specific Gene Expression In Vivo by Direct Gene Transfer into o the Arterial Wall," Science 249(4974):1285-1288.

Nabel, G.J. et al. (Dec. 1993). "Direct Gene Transfer with DNA-Liposome Complexes in Melanoma: Expression, Biologic Activity, and Lack of Toxicity in Humans," Proc. Natl. Acad. Sci. U.S.A. 90:11307-11311.

Nseyo, U.O. et al. (Oct. 1996). "Therapy of Superficial Bladder Cancer," Semi. In Oncol. 23(5):598-604.

Otsuji, M. et al. (Nov. 1996). "Oxidative Stress by Tumor-deprived Macrophages Suppresses the Expression of CD3 ? Chain of T-Cell Receptor Complex and Antigen-specific T-Cell Responses," Proc. Natl. Acad. Sci. U.S.A. 93:13119-13124.

Pang, L. et al. (1999). "Membrane Cholesterol Modulates Galanin-GaIR2 Interaction," Biochem. 38(37):12003-12011.

Patard, J.J. et al. (1998). "Immune Response Following Intravesical Bacillus Calmette-Guerin Instillations in Superficial Bladder Cancer: A Review," Urol. Res. 26:155-159.

Plautz, G.E. et al. (May 1993). "Immunotherapy of Malignancy by In Vivo Gene Transfer into Tumors," Proc. Nat. Acad. Sci. U.S.A. 90:4645-4649.

Rajewski, R.A. et al. (Nov. 1996). "Pharmaceutical Applications of Cyclodextrins. 2. In Vivo Drug Delivery," J. Pharm. Sci. 85(11):1142-1169.

Rodal, S.K. et al. (Apr. 1999). "Extraction of Cholesterol with Methyl-?-Cyclodextrin Perturbs Formation of Clathrin-coated Endocytic Vesicles," Mol. Biol. Cell 10:961-974.

Ruponen, M. et al. (1999). "Interactions of Polymeric and Liposomal Gene Delivery Systems with Extracellular Glycosaminglycans: Physicochemical and Transfection Studies," Biochem. et Biophys. Acta 1415:331-341.

Saito, S. et al. (Jul. 1994). "Immunotherapy of Bladder Cancer with Cytokine Gene-modified Tumor Vaccines," Can. Res. 54:3516-3520.

Salazar-Ontray, F. (1997). "Down-Regulation of the Expression and Function of the Transporter Associated with Antigen Processing in Murine Tumor Cell Lines Expressing IL-10," J. Immunology 159:3195-3202.

Sander, B. et al. (Aug. 1996). "Localization of IL-1, IL-2, IL-4, IL-8 and TNF in Superficial Bladder Tumors Treated with Intravesical Bacillus Calmette-Guerin," J. Urol. 156:536-541.

Schmidt-Wolf, G.D. et al. (Apr. 1995). "Cytokines and Gene Therapy," Immunology Today 16(4):173-175.

Seed, B. (Oct. 1987). "An LFA-3 cDNA Encodes a Phospholipid-linked Membrane Protein Homologous to its Receptor CD2," Nature 329:840-842.

Semple, S.C. et al. (1996). "Influence of Cholesterol on the Association of Plasma Proteins with Liposomes," Biochem. 35(8):2521-2525.

Song, Y.K. et al. (1997). "Characterization of Cationic Liposome-Mediated Gene Transfer In Vivo by Intravenous Administration," Hum.Gene Ther. 8(13):1585-1594.

Stephan, D.J. et al. (Oct. 1996). "A New Cationic Liposome DNA Complex Enhances the Efficiency of Arterial Gene Transfer In Vivo," Hum. Gene Ther. 7(15):1803-1812.

Sterman, D.H. et al. (May 1998). "Adenovirus-Mediated Herpes Simplex Virus Thymidine Kinase/Ganciclovir Gene Therapy in Patients with Localized Malignancy: Results of a Phase 1 Clinical Trial in Malignant Mesothelioma," Hum. Gene Ther. 9(7):1083-1092.

Stribling, R. et al. (Dec. 1992). "Aerosol Gene Delivery In Vivo," Proc. Natl. Acad. Sci. U.S.A. 89:11277-11281.

Sutton, M.A. et al. (1997). "Adenovirus-Mediated Suicide Gene Therapy for Experimental Bladder Cancer," J. Urol. 49(2):173-180.

Sutton, M.A. et al. (Sep. 2000). "In Vivo Adenovirus-Mediated Suicide Gene Therapy of Orthotopic Bladder Cancer," Mol. Ther. 2(3):211-217.

Syrigos, K.N. et al. (2003). "Clinical Significance of Heat Shock Protein-70 Expression in Bladder Cancer," Urology 61(3):677-680.

Szejtli, J. (1994). "Medicinal Applications of Cyclodextrins," Med. Res. Rev. 14(3):353-386.

Taniguchi, K. et al. (1999). "Systemic Immune Response After Intravesical Instillation of Bacille Calmette-Guérin (BCG) for Superficial Bladder Cancer," Clin. Exp. Immunol. 115:131-135.

Templeton, N.S. et al. (Jul. 1997). "Improved DNA: Liposome Complexes for Increased Systemic Delivery and Gene Expression," Nature Biotech. 15(7):647-652.

Tenjarla, S. et al. (Apr. 1998). "Preparation, Characterization, and Evaluation of Miconazole-Cyclodextrin Complexes for Improved Oral Topical Delivery," J. Pharm. Sci. 87(4):425-429.

Toda, M. et al. (May 1998). "In Situ Cancer Vaccination: An IL-12 Defective Vector/Replication-Competent Herpes Simplex Virus Combination Induces Local and Systemic Antitumor Activity," J. Immunology 160(9):4457-4464.

Torre-Amione, G. et al. (Feb. 1990). "A Highly Immunogenic Tumor Transfected with a Murine Transforming Growth Factor Type β1 cDNA Escapes Immune Surveillance," Proc. Natl. Acad. Sci. U.S.A. 87:1486-1490.

Vigneron, J.-P. et al. (Sep. 1996). "Guanidinium-Cholesterol Cationic Lipids: Efficient Vectors for the Transfection of Eukaryotic Cells," Proc. Natl. Acad. Sci. U.S.A. 93:9682-9686.

Von Der Leyen, H.E. et al. (Feb. 1995). "Gene Therapy Inhibiting Neointimal Vascular Lesion: In Vivo Transfer of Endothelial Cell Nitric Oxide Synthase Gene," Proc. Natl. Acad. Sci. U.S.A. 92:1137-1141.

Weiss, D.J. et al. (Sep. 1997). "In Situ Histochemical Detection of ?-Galactosidase Activity in Lung: Assessment of X-Gal Reagent in Distinguishing IacZ Gene Expression and Endogenous ?-Galactosidase Activity," Hum. Gene Ther. 8:1545-1554.

Werthman, P.E. et al. (Feb. 1996). "Adenoviral-P53 Gene Transfer to Orthotopic and Peritoneal Murine Bladder Cancer," J. Urol. 155:753-756.

Whartenby, K.A. et al. (Apr. 1995). "Gene-Modified Cells for the Treatment of Cancer," Pharm. Ther. 66(1):175-190.

Wheeler, C.J. et al. (Oct. 1996). "A Novel Cationic Lipid Greatly Enhances Plasmid DNA Delivery and Expression in Mouse Lung," Proc. Natl. Acad. Sci. U.S.A. 93(21):11454-11459.

Wu, Q. et al. (Oct. 1, 2003). "Nonviral Cytokine Gene Therapy on an Orthotopic Bladder Cancer Model," Clinical Cancer Research 9:4522-4528.

Wu, Q. et al. (Oct. 15, 2004). "Monitoring the Response of Orthotopic Bladder Tumors to Granulocyte Macrophage Colony-Stimulating Factor Therapy Using the Prostate-Specific Antigen Gene as a Reporter," Clinical Cancer Research 10:6977-6984.

Zabner, J. et al. (Aug. 1995). "Cellular and Molecular Barriers to Gene Transfer by A Cationic Lipid," J. Biol. Chem. 270(32):18997-19007.

Zhang, Y. et al. (1997). "Effects of Bacillus Calmette-Guérin and Interferon-?-2B on Human Bladder Cancer In Vitro," Int. J. Cancer 71:851-857.

Zhao, Q. et al. (1995). "Use of Cyclodextrin and its Derivatives as Carriers for Oligonucleotide Delivery," Anti. Res. and Devel. 5:185-192.

Zhu, N. et al. (Jul. 1993). "Systemic Gene Expression After Intravenous DNA Delivery into Adult Mice," Science 261(5118):209-211.

Lerner, S.P. ed. et al. (2006). *Textbook of Bladder Cancer*, Taylor & Francis Group: Oxon, United Kingdom, pp. 45-49.

\* cited by examiner

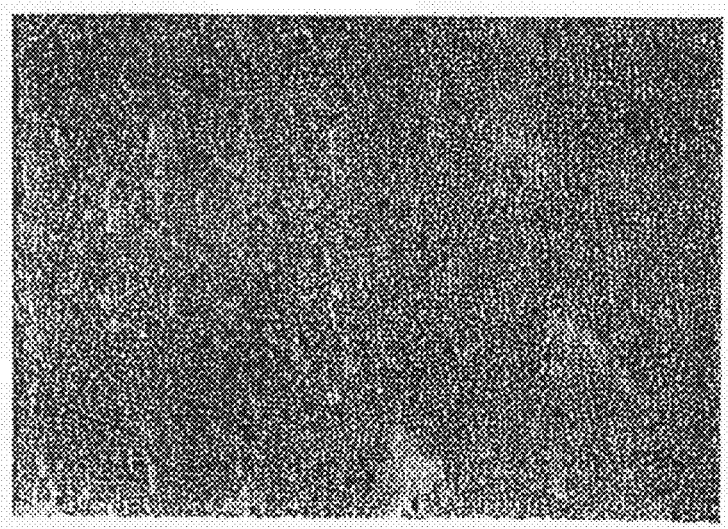
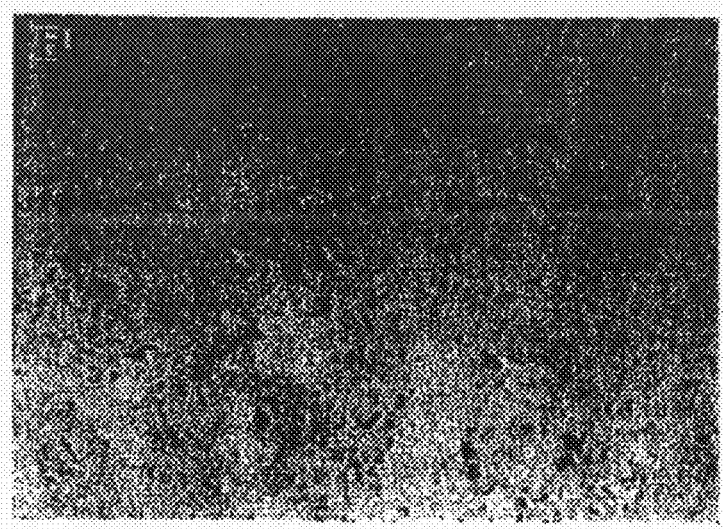
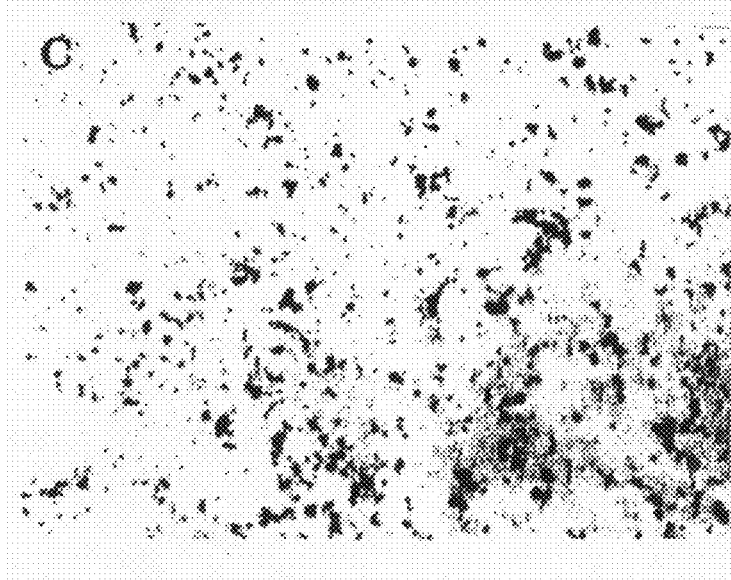
Fig. 1A
Fig. 1B
Fig. 1C

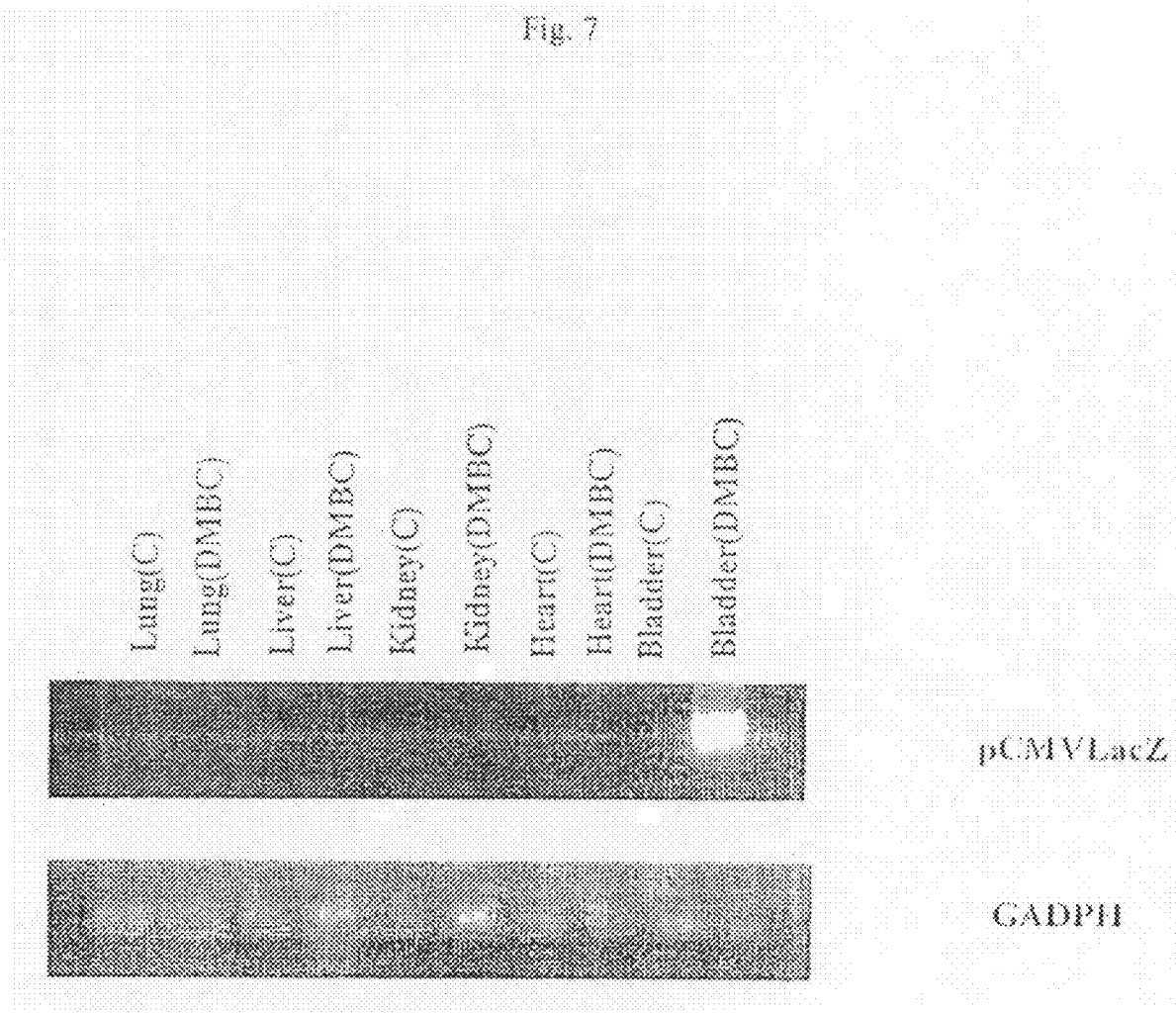

Fig. 8B
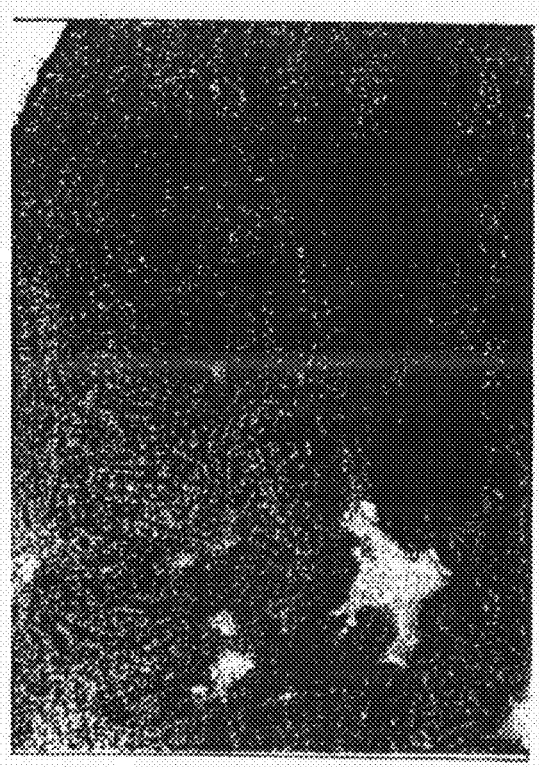

SEQUENCE LISTING

```
<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Synthesized primer

<400> SEQUENCE: 1
gccgaccgca cgccgcatcc agc                                             23

<210> SEQ ID NO 2
<211> LENGTH: 17
<212> TYPE: DNA
<213> ORGANISM: Artificial Sequence
<220> FEATURE:
<223> OTHER INFORMATION: Synthesized primer

<400> SEQUENCE: 2
cgccgcgcca ctggtgt                                                    17
```

```
<210> SEQ ID NO 3
<211> LENGTH: 15
<212> TYPE: DNA
<213> ORGANISM: Artificial Sequence
<220> FEATURE:
<223> OTHER INFORMATION: Synthesized primer

<400> SEQUENCE: 3
ctgcgacttc aacag                                                    15

<210> SEQ ID NO 4
<211> LENGTH: 16
<212> TYPE: DNA
<213> ORGANISM: Artificial Sequence
<220> FEATURE:
<223> OTHER INFORMATION: Synthesized primer

<400> SEQUENCE: 4
caccctgttg ctgtag                                                   16
```

METHODS AND COMPOSITIONS FOR DELIVERY OF PHARMACEUTICAL AGENTS

CROSS-REFERENCE TO RELATED APPLICATIONS

This application is a continuation of U.S. patent application Ser. No. 10/086,973, filed Mar. 1, 2002, now U.S. Pat. No. 7,320,963, which claims priority to PCT/SG00/00130, filed Sep. 1, 2000, which claims priority to Australian Provisional Application No. PQ2593/99, the entire contents of which are hereby incorporated by reference.

TECHNICAL FIELD

The present invention generally relates to the delivery of pharmaceutical agents into cells, particularly the delivery of polynucleotides into cells by non-viral methods, either in vitro or in vivo. The present invention further relates to delivery of pharmaceutical agents for the treatment of cancer, in particular the treatment of bladder cancer.

BACKGROUND OF THE INVENTION

Despite many recent advances in gene therapy methods, effective therapeutic delivery of genes into various cell types, in particular in vivo delivery, has not been achieved simply because methods are not available to cause delivery of therapeutically effective amounts of such genes into the particular cells of a patient in need of treatment. Efficient delivery of therapeutically sufficient amounts of genes, as well as other therapeutic molecules, often has proved difficult, if not impossible, since, for example, the cell membrane presents a selectively-permeable barrier. Additionally, even when genes, or other biologically active molecules, successfully enter targeted cells, they may be degraded, inappropriately transported or, in the case of genes, may fail to be transcribed properly.

One example of a target cell type for which effective delivery methods, in particular for gene therapy, are lacking is the urothelial cells of the bladder. Such methods would be particularly useful in the treatment of bladder cancer. Despite advances in endoscopic and intravesical chemotherapeutic procedures, superficial bladder cancer still has a high recurrence and progression rate (Nseyo U O, Lamm D L. (1996) *Semin. Oncol.* 5:598-604). Currently, the most successful treatment involves weekly instillation of 'live' Bacillus Calmette-Guerin (BCG) into the bladder for two hours (Morales, A. et al. (1976) *J. Urol.*, 116: 180-183; Brosman, S. A. (1992) *Urol. Clin. North Am.*, 19:557-564). Although effective, with routine response rates of 60-70%, side effects such as dysuria, haematuria, frequency and cystitis are common and sometimes severe (Lamm, D. L. (1992) *Urol. Clin. North Am.*, 19:565-572). Moreover, a significant number of patients do not respond to BCG therapy and toxicity is common. Exploration of the mechanism of BCG activation of the immune response has resulted in the identification of cytokines, co-stimulatory molecules and adhesion molecules which play important roles in facilitating the cytotoxic response against tumors (Taniguchi, K et al. (1999) *Clin. Exp. Immunol.*, 115: 131-5, 1999; Patard, J. J. et al. (1998) *Urol. Res.*, 26:155-9; Kurisu, K. et al. (1994) *Cancer Immunol. Immunother,* 39:249-53; Sander, B. et al. (1996) *J. Urology,* 156:536-41; Chow, N. H. et al. (1998) *Urology,* 52:1015-9; Jackson, A. M. et al. (1995) *Clin. Exp. Immunol.*, 99:369-75).

Superficial bladder cancers have some features that make them particularly attractive for in vivo gene therapy namely that tumors are often localized and therapeutic genes can be placed in direct contact with the tumor through simple intravesical administration. Further, the response of the tumor to treatment can be easily determined with cystoscopy and urine cytology. One of the major obstacles to successful transfection of the transitional cell epithelia is the presence of a glycosaminoglycan layer, which may act as a significant barrier the uptake of DNA complexes (Ruponen, M. et al. (1999) *Biochim. Biophys. Acta,* 1415: 331-41).

Viral expression vectors have been used to introduce specific genes locally to the bladder (Sutton, M. A. et al. (1997) *Urology,* 49: 173-80; Lee, S. S. et al. (1994) *Cancer Res.*, 54:3325-8). However, viral vectors have a number of limitations in a clinical setting such as immunogenicity and safety. A recent study by Li et al. has questioned the effectiveness of adenovirus-based gene therapy for bladder cancer owing to the differences in viral receptor levels observed in human bladder cancer cell lines (Li, Y. et al. (1999) *Cancer Res.*, 59:325-30).

An alternative method of gene therapy involves liposome-mediated delivery of DNA into cells. The advantage of a non-viral system is that it is not receptor dependent and should therefore be applicable to all tumors. Brigham et al. first reported delivery of DNA into tissues using cationic liposomes (Brigham, K. L. et al. (1989) *Am. J. Med. Sci.*, 298:278-81). Since then cationic lipids have been shown to be efficient carriers for localized and systemic delivery of DNA to tissues in vivo (Plautz, G. E. et al. (1993) *Proc. Natl. Acad. Sci. USA,* 9:4645-9; Nabel, G. J. et al. (1993) *Proc. Natl. Acad. Sci. USA,* 20:11307-11; Zhu, N. et al. (1993) *Science,* 261:209-11). Cationic liposomes have a number of important advantages over viral gene delivery systems in the clinical setting. These include the ability to use a range of gene constructs from simple plasmids to chromosomal fragments and fewer safety concerns. Their principal disadvantage, however, is their relatively low transfection efficiency when compared to viral techniques.

Accordingly, methods for increasing transfection efficiencies, particularly of urothelial cells, are still needed, as are general methods for delivering pharmaceutical agents to the bladder.

SUMMARY OF THE INVENTION

This invention provides improved methods for delivering pharmaceutical agents, in particular polynucleotides, into cells, in particular uroepithelial cells. It has now been found that use of solubilized cholesterol as an additive can enhance the transfection efficiency of DNA complexed with a cationic lipid, a cationic polymer or a dendrimer. Preferably, the cholesterol is solubilized using a cyclodextrin, preferably methyl-β-cyclodextrin. Although particularly preferred for transfection of urothelial cells either in vitro or in vivo, the transfection methods of the invention can be applied to the transfection of a variety of other cells types. Moreover, the enhancing effect of solubilized cholesterol on entry of DNA complexed with either a cationic lipid, a cationic polymer or a dendrimer into urothelial cells can be applied to the delivery of other types of pharmaceutical agents into urothelial cells, either in vitro or in vivo by intravascular delivery.

Accordingly, in one aspect, the invention provides a method for transfecting one or more polynucleotides into cells. The method involves combining (i) the polynucleotide (s) with (ii) a cationic lipid, a cationic polymer or a dendrimer, or combinations thereof, and (iii) a solubilized cholesterol preparation to form a transfection composition, and applying the transfection composition to cells, such that the cells are transfected with the polynucleotide(s). Preferably, the solubilized cholesterol preparation comprises cholesterol solubilized with a cyclodextrin. Preferably, the cyclodextrin is methyl-β-cyclodextrin. Other suitable cyclodextrins include alpha-cyclodextrin, beta-cyclodextrin, gamma-cyclodextrin, sulfated beta-cyclodextrin, tertiary amine beta-cyclodextrin, quaternary amine beta-cyclodextrin, 2-hydroxypropyl-beta-cyclodextrin, 2,6-di-O-methyl-beta-cyclodextrin, hydroxyethyl-beta-cyclodextrin, 6-deoxy-S-beta-D-galactopyranosyl-6-thio-cyclomalto-heptaose, sulfobutylether-beta-cyclodextrin, carboxymethyl-beta-cyclodextrin, carboxymethyl-ethyl-beta-cyclodextrin, diethyl-beta-cyclodextrin, dimethyl-beta-cyclodextrin, random methyl-beta-cyclodextrin, glucosyl-beta-cyclodextrin and maltosyl-beta-cyclodextin. A preferred cationic lipid is DOTAP, whereas a preferred dendrimer is Superfect. Other suitable cationic lipids and dendrimers include DOPE, DOTMA, DOGS, DODAB, DODAC, DOSPA, DC-Chol, DOIC, DOPC, DMRIE, PAMAM, polylysine, polyhistidine, polyarginine, polyethyleneimine, poly(4-vinylpyridine), poly(vinylamine), poly(4-vinyl-N-alkyl pyridinium halide), or combinations thereof. The method can be used to transfect a variety of polynucleotides, such as plasmid DNA, viral DNA, chromosomal fragments, antisense oligonucleotides, antisense phosphorothioate oligonucleotides, RNA molecules and ribozymes, or combinations thereof.

The transfection methods of the invention are preferably used with eukaryotic cells, more preferably mammalian cells and even more preferably urothelial cells. The transfection methods can be performed in vitro, e.g., wherein the transfection composition is applied to cells in culture. Alternatively, the methods can be performed in vivo by applying the transfection composition to cells in vivo. In a preferred embodiment, the transfection composition is applied to urothelial cells in vivo by intravesical delivery to a bladder of a subject.

In another aspect, the invention provides a method for delivering a pharmaceutical agent into urothelial cells of a subject. The method involves combining the pharmaceutical agent with a solubilized cholesterol preparation to form a pharmaceutical composition, and delivering the pharmaceutical composition intravascularly into the bladder of the subject, such that the pharmaceutical agent is delivered into urothelial cells of the subject. Preferably, the solubilized cholesterol preparation comprises cholesterol solubilized with a cyclodextrin. Preferably, the cyclodextrin is methyl-β-cyclodextrin. Other suitable cyclodextrins include alpha-cyclodextrin, beta-cyclodextrin, gamma-cyclodextrin, sulfated beta-cyclodextrin, tertiary amine beta-cyclodextrin, quaternary amine beta-cyclodextrin, 2-hydroxypropyl-beta-cyclodextrin, 2,6-di-O-methyl-beta-cyclodextrin, hydroxyethyl-beta-cyclodextrin, 6-deoxy-6-S-beta-D-galactopyranosyl-6-thio-cyclomalto-heptaose, sulfobutylether-beta-cyclodextrin, carboxymethyl-beta-cyclodextrin, carboxymethyl-ethyl-beta-cyclodextrin, diethyl-beta-cyclodextrin, dimethyl-beta-cyclodextrin, random methyl-beta-cyclodextrin, glucosyl-beta-cyclodextrin and maltosyl-beta-cyclodextrin. In a preferred embodiment, the pharmaceutical agent comprises (i) at least one polynucleotide and (ii) a cationic lipid, a cationic polymer or a dendrimer, or combinations thereof.

Yet another aspect of the invention pertains to a method for treating bladder cancer in a subject. The method involves combining a pharmaceutical agent with a solubilized cholesterol preparation to form a therapeutic composition, wherein the pharmaceutical agent has anti-cancer activity against bladder cancer cells, and delivering the therapeutic composition intravascularly into the bladder of a subject, such that bladder cancer cells of the subject are treated with the pharmaceutical agent. Preferably, the solubilized cholesterol preparation comprises cholesterol solubilized with a cyclodextrin. Preferably, the cyclodextrin is methyl-β-cyclodextrin. Other suitable cyclodextrins include alpha-cyclodextrin, beta-cyclodextrin, gamma-cyclodextrin, sulfated beta-cyclodextrin, tertiary amine beta-cyclodextrin, quaternary amine beta-cyclodextrin, 2-hydroxypropyl-beta-cyclodextrin, 2,6-di-O-methyl-beta-cyclodextrin, hydroxyethyl-beta-cyclodextrin, 6-deoxy-6-S-beta-D-galactopyranosyl-6-thio-cyclomalto-heptaose, sulfobutylether-beta-cyclodextrin, carboxymethyl-beta-cyclodextrin, carboxymethyl-ethyl-beta-cyclodextrin, diethyl-beta-cyclodextrin, dimethyl-beta-cyclodextrin, random methyl-beta-cyclodextrin, glucosyl-beta-cyclodextrin and maltosyl-beta-cyclodextrin.

A preferred pharmaceutical agent for treating bladder cancer comprises at least one polynucleotide and either a cationic lipid, a cationic polymer or a dendrimer, wherein the polynucleotide(s) imparts anti-cancer activity. For example, the polynucleotide(s) can comprise at least one expression vector encoding a protein selected from the group consisting of interleukins, interferons, colony stimulating factors, anti-angiogenic factors, anti-metastatic factors, membrane receptors and tumor suppressors. Preferred proteins include interleukin-1 (IL-1), interleukin-2 (IL-2), interleukin-6 (IL-6), interleukin-9 (IL-9), interleukin-11 (IL-11), interleukin-12 (IL-12), interleukin-13 (IL-13), interleukin-18 (IL-18), interferon-α, interferon-β, interferon-γ, granulocyte-macrophage colony stimulating factor (GMCSF), granulocyte colony stimulating factor (GCSF), macrophage colony stimulating factor (MCSF), heat shock protein (HSP), p53, anti-angiogenic factors, e.g., antagonists of vascular endothelial cell growth factor (VEGF) such as antisense molecules, anti-metastatic factors, e.g., tissue inhibitors of metalloproteinases (TIMPs), and factors that increase BCG activity, such as fibronectin receptors. Particularly preferred proteins include IL-2, GMCSF and interferon-γ, and combinations thereof.

The method of the invention for treating bladder cancer also can involve performing an additional anti-bladder cancer treatment on the subject. For example, a preferred additional anti-bladder cancer treatment that can be combined with the treatment method of the invention is Bacillus Calmette-Guerin (BCG) therapy.

Still another aspect of the invention pertains to transfection compositions. The invention provides a transfection composition comprising: at least one polynucleotide; either a cationic lipid, a cationic polymer or a dendrimer, and a solubilized cholesterol preparation. Preferably, the solubilized cholesterol preparation comprises cholesterol solubilized with a cyclodextrin. Preferably, the cyclodextrin is methyl-β-cyclodextrin. Other suitable cyclodextrins include alpha-cyclodextrin, beta-cyclodextrin, gamma-cyclodextrin, sulfated beta-cyclodextrin, tertiary amine beta-cyclodextrin, quaternary amine beta-cyclodextrin, 2-hydroxypropyl-beta-cyclodextrin, 2,6-di-O-methyl-beta-cyclodextrin, hydroxyethyl-beta-cyclodextrin, 6-deoxy-6-S-beta-D-galactopyranosyl-6-thio-cyclomalto-heptaose, sulfobutylether-beta-cyclodextrin, carboxymethyl-beta-cyclodextrin, carboxymethyl-ethyl-beta-cyclodextrin, diethyl-beta-cyclodextrin, dimethyl-beta-cyclodextrin, random methyl-beta-cyclodextrin, glucosyl-beta-cyclodextrin and maltosyl-beta-cyclodextrin. A preferred cationic lipid is DOTAP, whereas a preferred dendrimer is Superfect. Other suitable cationic lipids and dendrimers include DOPE, DOTMA, DOGS, DODAB, DODAC, DOSPA, DC-Chol, DOIC, DOPC, DMRIE, PAMAM, polylysine, polyhistidine, polyarginine, polyethyleneimine, poly(4-vinylpyridine), poly(vinylamine), poly(4-vinyl-N-alkyl pyridinium halide), or combinations thereof. The transfection composition can comprise one or more of a variety of polynucleotides, such as plasmid DNA, viral DNA, chromosomal fragments, antisense oligonucleotides, antisense phosphorothioate oligonucleotides, RNA-molecules and ribozymes, or combinations thereof.

BRIEF DESCRIPTION OF THE DRAWINGS

FIGS. 1A-1C are photographs of either untransfected cells or cells transfected with DOTAP or DMBC, comparing the level of expression of the pCMVlacZ reporter plasmid. Untransfected cells (FIG. 1A) did not stain with X-gal. A few cells were transfected with pCMVlacZ/DOTAP and these stained positive with X-gal (FIG. 1B). Transfection with pCMVlacZ/DMBC resulted in an increase in the number of X-gal positive cells (FIG. 1C). Thus, transfection efficiency increased following the addition of methyl-β-cyclodextrin containing cholesterol (MBC) to DOTAP (D).

FIG. 4A shows PCR amplification products. The lacZ gene was found in both the nuclear (N) and cytoplasmic (CY) fractions of cells transfected with DMBC but only in the cytoplasmic fraction for cells transfected with DOTAP (D). FIG. 4B shows a densitometric analysis of nuclear (N) and cytoplasmic (CY) fractions relative to GADPH.

FIG. 7 shows cellular localization of pCMVLacZ after transient transfection. Organs from untransfected mice are labelled C for control tissue. Organs harvested from mice transfected with the pCMVLacZ/DMBC complex are labelled DMBC. Absence of β-galactosidase gene in all organs except the bladder was confirmed by PCR.

FIG. 8Bi-8Biv are photographs showing the effect of exposure time on transfection efficiency in vivo. Bladders were exposed to the pCMVLacZ/DMBC complex for i) 15 min, ii) 30 min, iii) 60 min and iv) 120 min (Magnification ×40). More urothelial cells were stained with X-gal with time.

DETAILED DESCRIPTION OF THE INVENTION

Figure 1D:
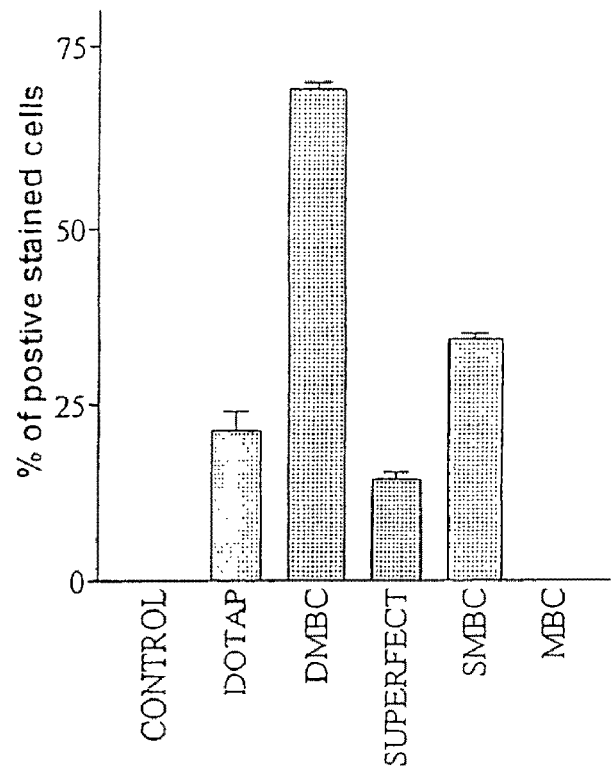
FIG. 1D is a bar graph showing the effect of MBC on conventional transfection agents. Cells transfected with DOTAP+methyl-3-cyclodextrin containing cholesterol (DMBC) or Superfect+methyl-β-cyclodextrin containing cholesterol (SMBC) showed an increase in the number of cells staining positive for β-gal activity compared to DOTAP or Superfect alone. MBC did not enhance the uptake of naked DNA.

Throughout this disclosure, various publications, patents and published patent applications are referenced by an identifying citation. The disclosures of these publications, patents and published patent applications are hereby incorporated by reference into the present disclosure to more fully describe the state of the art to which this invention pertains.

So that the invention may be more readily understood, certain terms are first defined.

As used herein, the various forms of the term "transfect" (e.g., "transfecting", "transfected") are intended to refer to the process of introducing a polynucleotide molecule from an exterior location into the interior of a cell.

As used herein, the term "polynucleotide molecule" is intended to encompass molecules comprised of two or more covalently linked nucleotide bases, including deoxyribonucleic acid (DNA) molecules and ribonucleic acid (RNA) molecules. The nucleotides forming the polynucleotide molecule typically are linked to each other by phosphodiester linkages, although the term "polynucleotide molecule" is also intended to encompass nucleotides linked by other linkages, such as phosphorothioate linkages. Nonlimiting examples of polynucleotide molecules include plasmid DNA, viral DNA, chromosomal fragments, antisense oligonucleotides, antisense phosphorothioate oligonucleotides, RNA molecules and ribozymes.

As used herein, the term "cationic lipid" is intended to refer to molecules comprised of at least one, and most typically two, fatty acid chains and a positively charged polar head group. Typical cationic lipids have either dodecyl ($C_{12}$) or hexadecyl (cetyl, $C_{16}$) fatty acid chains, although the term "cationic lipid" also is intended to encompass lipids with fatty acid chains of other lengths. Nonlimiting examples of cationic lipids include:

DOTAP (1,2-diacyl-3-trimethylammonium propane)
DOPE (dioleoyl phosphatidylethanolamine)
DOTMA ([2,3-bis(oleoyl)propyl]trimethyl ammonium chloride)
DOGS (dioctadecyl amido glycyl spermine)
DODAB (dioctadecyl diammonium bromide)
DODAC (dioctadecyl diammonium chloride)
DOSPA (2,3 dioleoyloxy-N-[sperminecarboxaminoethyl]-N—N-dimethyl-1-propanaminium)
DC-Chol (3β-[N-(n',N'-dimethylaminoethane)-carbamoyl]cholesterol, dioleoyl)
DOIC (1-[2-(oleoyloxy)-ethyl]-2-oleoyl-3-(2-hydroxyethyl) imidazolinium chloride)
DOPC (dioleoyl phosphatidylcholine)
DMRIE (dimyristooxypropyl dimethyl hydroxyethyl ammonium bromide)

As used herein, the term "cationic polymer" is intended to refer to positively charged polymers having the capacity to condense nucleic acid (e.g., DNA). Cationic polymers include polyelectrolytes and cationic polypeptides. Nonlimiting examples of cationic polymers include polylysine, polyhistidine, polyarginine, polyethyleneimine (PEI), poly(4-vinylpyridine), poly(vinylamine) and poly(4-vinyl-N-alkyl pyridinium halide).

As used herein, the term "dendrimer" is intended to refer to cationic starburst polymers. These are spherical polymers that originate from an ammonium core by spherical growth in layers. Nonlimiting examples of dendrimers include Superfect and PAMAM.

As used herein, the term "cholesterol" is intended to refer to a naturally-occurring steroid alcohol (sterol) having four fused rings, as well as its esters with long chain fatty acids, and analogues thereof that retain the ability to modulate membrane fluidity. Cholesterol and cholesterol esters are components of plasma lipoproteins and the outer cell membrane of animal cells, and have the ability to modulate membrane fluidity. Cholesterol analogues that retain the ability to modulate membrane fluidity are known in the art (see e.g., Gimpl, G., et al. (1997) *Biochemistry* 36:10959-10974) and include, for example, 5-cholestene, 5-pregnen-3β-ol-20-one, 4-cholesten-3-one and 5-cholesten-3-one.

As used herein, the term "solubilized cholesterol preparation" is intended to refer to a preparation in which cholesterol has been water solubilized using a solubilizing agent that increases the aqueous solubility of the cholesterol (i.e., the water solubility of the solubulized cholesterol preparation is higher than the water solubility of cholesterol alone). The solubilizing agent typically is a water soluble compound that has a cavity into which lipophilic molecules can be packaged. Preferred solubilizing agents are cyclodextrins. Solubilization of the cholesterol (e.g., incorporation into a solubilizing agent such as a cyclodextrin) can be monitored by radiolabeling the cholesterol, e.g., [1,2,6,7-3H(N)]cholesterol (commercially a England Nuclear), see for example Pang, L. et al. (1999) *Biochemistry* 38:12003-12011. The term "solubilized cholesterol preparation" is not intended to refer to cholesterol incorporated into the bilayers of a liposome.

As used herein, the term "cyclodextrin" is intended to refer to oligosaccharide cyclic shaped torus molecules having a hydrophilic outer surface and a hydrophobic central cavity, wherein this hydrophobic central cavity is capable of carrying lipophilic substances (e.g., cholesterol). "Cyclodextrins" include molecules having 6, 7 or 8 glucopyranose units (alpha-, beta- and gammacyclodextrins, respectively), as well as larger rings (cyclodextrins containing from 9-13 glucopyranose units have been isolated), although beta-cyclodextrins are preferred for use in the present invention. The term "cyclodextrin" is also intended to encompass derivatives of alpha-, beta- and gamma-cyclodextrins (or even larger rings), non-limiting examples of which include sulfated beta-cyclodextrin, tertiary amine beta-cyclodextrin, quaternary amine beta-cyclodextrin, 2-hydroxypropyl-beta-cyclodextrin, 2,6-di-O-methyl-beta-cyclodextrin, hydroxyethyl-beta-cyclodextrin, 6-deoxy-6-S-beta-D-galactopyranosyl-6-thio-cyclomalto-heptaose, sulfobutylether-beta-cyclodextrin, carboxymethyl-beta-cyclodextrin, carboxymethyl-ethyl-beta-cyclodextrin, diethyl-beta-cyclodextrin, dimethyl-beta-cyclodextrin, random methyl-beta-cyclodextrin, glucosyl-beta-cyclodextrin and maltosyl-beta-cyclodextrin. A preferred cyclodextrin for use in the invention is methyl-β-cyclodextrin. The structure and pharmaceutical applications of cyclodextrins are reviewed in Szejtli, J. (1994) *Med. Res. Reviews* 14:353-386 and Rajewski, R. A. and Stella, V. J. (1996) *J. Pharm. Sci.* 85:1142-1169.

As used herein, the term "transfection composition" refers to a composition resulting from the combination of a polynucleotide, either a cationic lipid or a dendrimer, and a solubilized cholesterol preparation.

As used herein, the term "pharmaceutical agent" is intended to encompass compounds having pharmaceutical activity, nonlimiting examples of which include polynucleotides; proteins, polypeptides, peptides, chemotherapeutic agents, antibiotics and the like.

As used herein, the term "therapeutic composition" is intended to refer to a composition formed by combining at least one pharmaceutical agent and a solubilized cholesterol preparation, although the therapeutic composition can contain additional components (e.g., additional pharmaceutical agents, a cationic lipid, a dendrimer or other component(s) that enhance the delivery or therapeutic activity of the therapeutic composition).

As used herein, the term "subject" is intended to refer to living organisms that may be in need of treatment with pharmaceutical agents, e.g., in need of treatment for cancer, such as bladder cancer. Preferred subjects are mammals. Examples of subjects include humans, monkeys, dogs, cats, mice, rats, cows, horses, goats and sheep. Subjects also include other vertebrates, such as fish and birds (e.g., chickens).

As used herein, the term "anti-cancer activity" is intended to mean that a pharmaceutical agent has an ability to inhibit the growth, viability or metastasis of cancer cells, either directly (i.e., by acting directly on the cancer cells, such as a chemotherapeutic agent that is toxic to cancer cells) or indirectly (e.g., by stimulating an immune response to the cancer cells).

As used herein, the term "treatment" is intended to refer to an alleviation of one or more symptoms of the disease being treated.

As used herein, the term "therapeutically effective amount" is intended to refer to an amount (e.g., of a pharmaceutical agent) sufficient to achieve treatment of a disease being treated.

As used herein, the term "bacillus Calmette-Guerin (BCG) therapy" is intended to refer to a treatment regimen for bladder cancer in which BCG is administered intravesically into the bladder to stimulate an immune response.

The present invention is based, at least in part, on the discovery that solubilized cholesterol can be used as an additive to improve the transfection efficiency of cells. A preferred solubilizing agent for the cholesterol is a cyclodextrin, such as methyl-β-cyclodextrin. Experiments showed that methyl-β-cyclodextrin containing cholesterol by itself does not improve the transfection of naked DNA but in conjunction with a cationic lipid (DOTAP) it enhances transfection. In vitro, this addition gave rise to a 3.8-fold increase in transfected cells compared to cationic lipid (DOTAP) alone (see Example 1). In vivo, bladder epithelial cells facing the lumen were successfully transfected, something that couldn't be achieved with cationic lipid alone (see Example 6). When the cationic lipid used is DOTAP, optimum transfection was obtained with a DOTAP-DNA ratio of 2.7:1 (wt:wt) and a DOTAP to cholesterol ratio of 6:1 (wt:wt). Crook et al using a mixture of DOTAP and cholesterol found that transfection was optimum when a ratio of 1:1 (wt:wt) of DOTAP:cholesterol was used (Crook, K et al. (1998) *Gene Ther.* 5:137-43). Their data indicated that increasing cholesterol increased the transfection efficiency in the presence of serum. However, using this combination of DOTAP:cholesterol there was very little transfection of the murine urothelial cell line MB49 although COS-7 cells were efficiently transfected.

The methyl-β-cyclodextrin/cholesterol (MBC) complex is capable of donating cholesterol to the cell membrane. Although not intending to be limited by mechanism, the donation of cholesterol would affect the fluidity/rigidity and permeability of the cell membrane. Cholesterol levels in membranes have been shown to affect the sorting of GPI anchored proteins in endosomes, with depletion increasing the recycling of these proteins via endosomes (Rodal, S. K et al. (1999) *Mol. Biol. Cell.* 10:961-74). It is also possible that the DOTAP/methyl-β-cyclodextrin/cholesterol (DMBC) complex donates cholesterol to the DOTAP molecules affecting the structure of the DOTAP:DNA complexes formed. Beta cyclodextrins have been shown to improve the internalization of adenoviruses by intestinal cells (Croyle, M. A. et al. (1998) *Pharm. Res.* 15:1348-1355). The improved uptake was attributed to the ability of cyclodextrins to disrupt cell membranes. None of the cyclodextrins used in that study carried cholesterol. Using only methyl-β-cyclodextrin by itself in combination with DOTAP and DNA there was no transfection of murine bladder epithelial cells, indicating the importance of the cholesterol packaged in the cyclodextrins for the increased transfection efficiency provided by the present invention.

In a recent study, Zabner and co-workers analysed the mechanism of gene delivery mediated by cationic lipids and identified the movement of plasmid DNA from the cytoplasm to the nucleus as the limiting factor for successful gene transfer (Zabner, J. et al. (1995) *J. Biol. Chem.*, 270:18997-9007). In the present invention, it was found that although the inclusion of cholesterol enhanced transfection efficiency, it had little effect on the uptake of plasmid DNA by cells. However, it was found that with DMBC, plasmid DNA was found in the nucleus (see Example 4), suggesting that the inclusion of DMBC may play a role in the escape of DNA from endosomes, perhaps avoiding degradation in lysosomes.

In the present system, expression of a transfected gene in urothelial cells can be observed in vivo up to a month after the transfection event. This may be related to the slower turnover of urothelial cells in vivo, as gene expression was quickly lost in vitro after multiple cell replications. Morris, B. D. et al., (*J. Urol.*, (1994) 152:506-509), who used adenoviruses to transfect the bladder, showed that gene expression was evident for at least 7 days. Harimoto et al. (*Br. J. Urol.* (1998) 81:870-874) showed that gene expression was observed up to 10 days with HVJ-liposomes and up to two weeks with a single particle gun bombardment. Thus the DMBC transfection system of the present invention is as, if not more, durable than the presently favored techniques for in vivo bladder transfection.

A two-hour exposure of cells to the DMBC/DNA complex showed no effect on cell proliferation (see Example 5). MBC by itself did not cause a decrease in cell proliferation after a 24 h exposure but DOTAP appeared to do so. However this was not statistically significant. The anti-proliferative effects of prolonged exposure may be advantageous, as it would serve to enhance the therapeutic gene mediated killing of tumor cells. A study showed that when methyl-β-cyclodextrin was used by itself, it had an anti-tumor effect of human'tumor xenografts in athymic nude mice (Grosse, P. Y. et al. (1998) *Br. J. Cancer* 78:1165-9). This effect is likely related to the efflux of cholesterol from cells.

Intravesical instillation of the DMBC/DNA complex, for just two hours, was sufficient to maximise exposure of the urothelium to the liposome/DNA complex and to ensure efficient transfection (see Example 7). Expression of a reporter gene (β-galactosidase) was confined to the bladder. Morris, B. D. et al. (*J. Urol.* (1994) 152:506-509), who used adenoviruses to transfect the bladder, made a similar observation indicating that this containment is probably a result of the architecture of the bladder and not because of the delivery system used.

The transfection system of the invention also has been shown to be effective in delivering cytokine genes in vivo for the eradication of tumors (see Example 9).

In view of the foregoing, one aspect of the invention pertains to methods for transfecting at least one polynucleotide into cells. As described further in the Examples, the use of solubilized cholesterol enhances the transfection efficiency of polynucleotides complexed with agents such as cationic lipids, cationic polymers and dendrimers. Accordingly, in one aspect, the invention provides a method for transfecting at least one polynucleotide into cells, the method comprising:
combining:
(i) at least one polynucleotide;
(ii) a cationic lipid, a cationic polymer or a dendrimer, or combinations thereof; and
(iii) a solubilized cholesterol preparation
to form a transfection composition; and
applying the transfection composition to cells, such that the cells are transfected with the polynucleotide.

Preferably, the solubilized cholesterol preparation comprises cholesterol solubilized with a cyclodextrin, most preferably methyl-β-cyclodextrin. Other suitable cyclodextrins include those listed above. Cyclodextrins can be obtained from commercially available sources. A preferred cationic lipid is DOTAP. A preferred dendrimer is Superfect. Other suitable cationic lipids, cationic polymers and dendrimers include those listed above. Cationic lipids, cationic polymers and dendrimers can be obtained from commercially available sources. The transfection composition may include one type of reagent (ii), i.e., either a cationic lipid, a cationic polymer or a dendrimer, or, alternatively, reagent (ii) may be a combination, such as both a cationic lipid and a cationic polymer, or two different types of cationic lipids or two different types of cationic polymers. When combining the reagents (i), (ii) and (iii), preferably the solubilized cholesterol preparation is mixed with the cationic lipid, cationic polymer or dendrimer immediately prior to the addition of the polynucleotide(s) and the mixture is then incubated for a period of time, e.g., 15 minutes at room temperature, to form the transfection composition.

The amounts of each reagent used may vary depending on conditions such as which particular reagents are chosen and what cell type is to be transfected. However, optimal transfection conditions can be determined by standard methods, such as using the transfection system described in the examples. For example, the optimal ratio of cationic lipid (or cationic polymer or dendrimer) to solubilized cholesterol may differ for different cell types, although a ratio of 1:2 (DOTAP:MBC) was found to be optimal for urothelial cells in vitro. A nonlimiting range of ratios of cationic lipid (or cationic polymer or dendrimer) to solubilized cholesterol is 2:1 to 1:3 (w/w). When preparing the solubilized cholesterol preparation (e.g. methyl-β-cyclodextrin/cholesterol, or MBC), a preferred proportion of cholesterol to cyclodextrin is 50 mg cholesterol to 600 mg cyclodextrin (methyl-β-cyclodextrin) (i.e., 1:12 w/w cholesterol:cyclodextrin), although again this proportion may be optimized depending upon the specific reagents used and conditions involved. A nonlimiting range of ratios of cholesterol to cyclodextrins is 1:1 to 1:20. The amount of polynucleotide used also can be varied depending on the reagents used and host cells to be transfected. A nonlimiting range for the amount of polynucleotide (e.g., DNA) used is 0.1 to 100 μg, more preferably 1-50 μg. A nonlimiting range for the amount of cationic lipid is 1 to 200 μg, preferably 10-50 μg. A nonlimiting range for the amount of dendrimer (e.g., Superfect) is 1 to 300 μg, preferably 5-25 μg. For in vivo applications, the amount of each reagent likely would need to be increased from the preferred amounts set forth above.

A nonlimiting example of preferred reagent amounts when DOTAP is used as the cationic lipid are: 7.5 μg DNA+20 μg DOTAP+40 μg of methyl-β-cyclodextrin solubilized cholesterol. A nonlimiting example of preferred reagent amounts when Superfect is used as the dendrimer are: 2 μg DNA+22.5 μg Superfect+10 μg of methyl-β-cyclodextrin solubilized cholesterol.

The transfection method of the invention can be used to transfect a variety of different polynucleotides, such as plasmid DNA, viral DNA, chromosomal fragments, antisense oligonucleotides, antisense phosphorothioate oligonucleotides, RNA molecules and ribozymes, or combinations thereof. For gene therapy purposes, the polynucleotide(s) typically is an expression vector (described in further detail below) that encodes a protein to be provided for therapeutic benefit. The transfection method preferably is used to transfect eukaryotic cells, more preferably mammalian cells. The transfection method is particularly effective in transfecting urothelial cells, which remain resistant to many other types of transfection methods. The transfection method can be carried out in vitro, e.g., by applying the transfection composition to cells in culture. The time period for contacting the transfection composition with the cells in culture can be optimized by standard methods. A nonlimiting example of a transfection time in vitro is 48 hours, followed by washing the cells (e.g., with phosphate buffered saline). Alternatively, the transfection method can be carried out in vivo, by applying the transfection composition to cells in vivo. In a preferred embodiment, the transfection composition is applied to urothelial cells in vivo by intravesical delivery (e.g., via a catheter) to a bladder of a subject. Other target tissues for transfection in vivo include, for example, stomach, muscle, lungs, epithelial cells, colon, uterus, intestine, heart, kidney, prostate, skin, eye, brain, penile tissue and nasal tissue.

In another aspect, the invention provides a method for delivering a pharmaceutical agent into urothelial cells of the bladder, based on the ability of solubilized cholesterol to enhance uptake of material by urothelial cells. Accordingly, the invention provides a method for delivering a pharmaceutical agent into urothelial cells of a subject, the method comprising:

combining the pharmaceutical agent with a solubilized cholesterol preparation to form a pharmaceutical composition; and delivering the pharmaceutical composition intravascularly into the bladder of the subject, such that the pharmaceutical agent is delivered into urothelial cells of the subject.

Preferably, the solubilized cholesterol preparation comprises cholesterol solubilized with a cyclodextrin, most preferably methyl-β-cyclodextrin. Other suitable cyclodextrins include those listed above. The pharmaceutical agent can be, for example, at least one polynucleotide and a cationic lipid, cationic polymer or a dendrimer. Alternatively, the pharmaceutical agent can be, for example, a chemotherapeutic agent, an antibiotic, an interferon, an interleukin, a colony stimulating factor, an anti-angiogenic factor, an anti-metastatic factor, a membrane receptor or other agent with therapeutic activity. When the pharmaceutical agent is a polynucleotide, a preferred cationic lipid is DOTAP, whereas a preferred dendrimer is Superfect. Other suitable cationic lipids, cationic polymers and dendrimers include those listed above.

In another aspect, the invention provides methods of treating bladder cancer in a subject, the method comprising:

combining a pharmaceutical agent with a solubilized cholesterol preparation to form a therapeutic composition, wherein the pharmaceutical agent has anti-cancer activity against bladder cancer cells; and delivering the therapeutic composition intravascularly into the bladder of a subject, such that bladder cancer cells of the subject are treated with the pharmaceutical agent.

Preferably, the solubilized cholesterol preparation comprises cholesterol solubilized with a cyclodextrin, most preferably methyl-β-cyclodextrin. Other suitable cyclodextrins include those listed above. The pharmaceutical agent can be, for example, at least one polynucleotide and a cationic lipid, cationic polymer or a dendrimer. Preferably, the pharmaceutical agent is delivered in therapeutically effective amounts. When the pharmaceutical agent is a polynucleotide(s), a preferred cationic lipid is DOTAP, whereas a preferred dendrimer is Superfect. Other suitable cationic lipids, cationic polymers and dendrimers include those listed above.

The polynucleotide preferably comprises at least one expression vector encoding a protein(s) of therapeutic benefit in the treatment of bladder cancer. An expression vector comprises a polynucleotide in a form suitable for expression of the polynucleotide in cells to be transfected, which means that the recombinant expression vector includes one or more regulatory sequences, usually selected on the basis of the type of cells to be transfected, which is operatively linked to the polynucleotide to be expressed. Within a recombinant expression vector, "operably linked" is intended to mean that the polynucleotide of interest is linked to the regulatory sequence(s) in a manner which allows for expression of the polynucleotide (e.g., transcription/translation in a host cell when the vector is introduced into the host cell). The term "regulatory sequence" is intended to includes promoters, enhancers and other expression control elements (e.g., polyadenylation signals). Such regulatory sequences are well known in the art and are described, for example, in Goeddel; Gene Expression Technology: Methods in Enzymology 185, Academic Press, San Diego, Calif. (1990). Regulatory sequences include those that direct constitutive expression of a polynucleotide in many types of host cell and those which direct expression of the polynucleotide only in certain host cells (e.g., tissue-specific regulatory sequences). It will be appreciated by those skilled in the art that the design of the expression vector may depend on such factors as the choice of the host cell to be transformed, the level of expression of protein desired, etc.

Examples of mammalian expression vectors include pMex-NeoI, pCDM8 (Seed, B., (1987) Nature 329:840) and pMT2PC (Kaufman et al. (1987), EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. Alternatively, mammalian expression vectors capable of directing expression of a polynucleotide preferentially in a particular cell type can be used (i.e., an expression vector comprising tissue-specific regulatory elements) and are well known in the art.

Examples of suitable proteins to be expressed by an expression vector in the bladder for treatment of bladder cancer include interleukins, interferons, colony stimulating factors, anti-angiogenic factors, anti-metastatic factors, membrane receptors and tumor suppressors. Preferred proteins include interleukin-1 (IL-1), interleukin-2 (IL-2), interleukin-6 (IL-6), interleukin-9 (IL-9), interleukin-11 (IL-11), interleukin-12 (IL-12), interleukin-13 (IL-13), interleukin-18 (IL-18), interferon-$\alpha$, interferon-$\beta$, interferon-$\gamma$, granulocyte-macrophage colony stimulating factor (GMCSF), granulocyte colony stimulating factor (GCSF), macrophage colony stimulating factor (MCSF), heat shock protein (HSP), p53, anti-angiogenic factors, e.g., antagonists of vascular endothelial cell growth factor (VEGF) such as antisense molecules, anti-metastatic factors, e.g., tissue inhibitors of metalloproteinases (TIMPs), and factors that increase BCG activity, such as fibronectin receptors, interleukins, interferons, colony stimulating factors and tumor suppressors. Preferred proteins to be expressed are IL-2, GMCSF or interferon-$\gamma$, or combinations thereof (e.g., at least two of IL-2, GMCSF and interferon-$\gamma$).

Alternatively, the pharmaceutical agent can be, for example, a chemotherapeutic agent, an antibiotic, an interferon, an interleukin, a colony stimulating factor or other agent with therapeutic activity.

The method of the invention for treating bladder cancer can be combined with one or more additional anti-bladder cancer treatment methods. A preferred additional treatment method is BCG therapy. Other examples of additional cancer treatments include chemotherapy and radiation therapy.

In another aspect, the invention also provides transfection compositions. The transfection compositions of the invention comprise:

(i) at least one polynucleotide;

(ii) a cationic lipid, cationic polymer or a dendrimer, or combinations thereof; and (iii) a solubilized cholesterol preparation.

Preferably, the solubilized cholesterol preparation comprises cholesterol solubilized with a cyclodextrin, most preferably methyl-$\beta$-cyclodextrin. Other suitable cyclodextrins include those listed above. A preferred cationic lipid is DOTAP, whereas a preferred dendrimer is Superfect. Other suitable cationic lipids, cationic polymers and dendrimers include those listed above. The transfection compositions of the invention can be provided as a packaged formulation, e.g., wherein each component reagent is provided in a container means. The packaged formulation further may include instructions for using the transfection composition to transfect cells.

The present invention is further illustrated by the following examples, which should not be construed as limiting in any way.

Specific materials and methods used in the following examples are described below:

Materials and Methods

PCMVlacZ was obtained from Clontech, Palo Alto, Calif., USA. The murine transitional cell carcinoma cell line MB49, was obtained from Dr. Timothy Ratliff at the University of Iowa. Plasmid DNA was prepared using Endofree plasmid Qiagen kits (Qiagen GmbH, Germany). Fugene was purchased from Roche Diagnostics, Mannheim Germany, Superfect from Qiagen GmbH, Germany, DEAE dextran from Promega, Madison USA and Calcium phosphate from Merck, Frankfurt, Germany.

In Vitro Assay for DMBC Transfection Efficiency $2 \times 10^5$ cells were plated on coverslips, in 6 well tissue culture plates in RPMI 1640 supplemented with 10% FBS (Biosciences, Australia), 2 mM L-glutamine, 50 U/ml penicillin and 0.05 mg/ml streptomycin (Sigma Chemical Company St. Louis, Mo., USA). Cells were washed twice with 1×PBS and transfected with 7.5 µg of pCMVlacZ complexed with 20 µg of DOTAP (Roche Diagnostics, Mannheim Germany) and 40 µg of methyl-$\beta$-cyclodextrin solubilized cholesterol (Sigma). The complexes were formed by making up the DNA and DMBC to 16511 with 20 mM Hepes buffer (GibcoBRL, Rockville, Md., USA) and mixing for 15 min. This was made up to 1 ml with RPMI 1640 media, and added to wells for the appropriate length of time then washed and replaced with 3 ml of fresh RPMI 1640 media. After 48 h, the cells were washed with PBS, fixed and stained as described in Weiss, D. J. et al. (1997) Hum. Gene Ther. 8:1545-54. The average number of blue colonies, relative to the total number of cells in four quadrants at ×100 magnification, was used to determine the transfection efficiency. Transfections were performed in duplicates and repeated twice.

Proliferation Assays

Proliferation was assayed by measuring [$^{14}$C]-thymidine incorporation. $1 \times 10^4$ cells were plated per well in a 96 well flat-bottomed tissue culture plate (Nunc, Rosklide, Denmark) and transfected at optimal conditions as described above for the appropriate length of time (2 h and 24 h exposure), washed and incubated with fresh RPMI 1640 at 37° C. After 32 h, supernatants were removed, and cells were rinsed with 1×PBS. Triplicate wells were incubated with 6 ml, [$^{14}$]-thymidine (specific activity 56.5 mCi/mmol; Du Pont, Wilmington, Del., USA) for 16 h. The samples were harvested as described in Zhang, Y. et al. (1997) Int. J. Cancer 71:851-7. [$^{14}$C]-thymidine incorporation was expressed as a percentage of the incorporation in control cells, which consisted of untransfected cells. The non-parametric Mann-Whitney U test was used to calculate statistical significance. Probability values of $p<0.05$ were considered statistically significant.

Detection of Reporter Gene Expression In Vivo After Intravesical Delivery of DNA-DMBC 5-7 week old-female C57BL6 mice were anaesthetized; their bladders were catheterized with 24 G i.v. catheter and flushed with 1×PBS. The DMBC and DNA complex were mixed for 15 min as described above. The final mix was made up to a final volume of 465 µl with 1×PBS for easy instillation and introduced intravesically. Transfection exposure times of 15 min, 30 min, 1 h or 2 h were evaluated. At different time points the bladders were flushed with 1×PBS to remove DNA/DMBC complex. The mice were sacrificed 48 h after treatment. Experiments were done in duplicates.

Histochemistry

Bladders, lungs, kidneys, heart, liver and spleen were removed and snap frozen in liquid nitrogen (Werthman, P. E. et al. (1996) *J. Urol.* 55:53-6). Cryostat sections of 6 µM in thickness were fixed in 1.25% glutaraldehyde for 10 min at 4° C. followed by incubation with X-gal for 4 h at 37° C. and were counterstained with haematoxylin.

Performing PCR on Organs

To detect the presence of the transfected plasmid PCR primers unique to the lacZ gene were employed. The upstream primer used was 5'-GCCGACCGCACGCCG-CATCCAGC-3' (SEQ ID NO:1) and the downstream primer was 5'-CGCCGCGCCACTGGTGT-3' (SEQ ID NO: 2). PCR was carried out in a total volume of 25 µl containing 100 ng of genomic DNA, 2 µl (2.5 Mm) of dNTPs (New England Biolabs, Beverly, USA), 2.5 µl of (10×) reaction buffer, 1 µl of each primer (10 uM) and 1 µl (2 U) of Taq polymerase (Finnzymes, Espoo, Finland). The PCR program was as follows: 94° C. for 30 s, followed by, 60° C. for 30 s and 72° C. for 30 s for 40 cycles. GADPH was used as a control for PCR analysis. The primer sequences for GADPH are upstream primer 5'-CTGCGACTTCAACAG-3' (SEQ ID NO: 3) and downstream primers 5'-CACCCTGTTGCTGTAG-3' (SEQ ID NO: 4). The PCR program was as follows: 94° C. for 30 s, 58° C. for 30 s and 72° C. for 30 s for 40 cycles. Amplified DNA were analysed by electrophoresis on a 1% agarose gel and visualized with ethidium bromide under UV light. Densitometry scanning was carried out using the Image master VDS software and bands were analysed using the Analytical Imaging System software (Imaging Research Inc., Ontario, Canada).

ONPG Assay for Transfection

Transfected cells were washed twice with 1×PBS and then lysed with 150 µl of lysis buffer. The protein content of the lysates was measured by the Micro BCA Protein assay (Pierce, Rockford, Ill., USA) with bovine serum albumin as a standard. Cell protein lysates were assayed in a reaction mixture containing 4 mg/ml of ONPG and incubated at 37° C. for 1 h. Reactions were stopped by the addition of 500 µl 1 M $Na_2CO_3$ and the absorbance at 420 nm was measured.

Nuclear and Cytoplasmic Analysis by PCR

Nuclear and cytoplasmic fractionation of transfected cells was carried out using gentle lysis with TNE buffer (10 mM Tris, pH (pH8), 1 mM EDTA, 100 mM NaCl, 1% Igepecal) and left on ice for 10 min followed by centrifugation at 7K for 5 min at 4° C. in a microfuge. The supernatant so produced was labelled the cytoplasmic extract and was transferred to a fresh tube. The nuclear extract were prepared by treatment with a proteinase K digestion (100 mM, NaCl, 10 Mm Tris, pH8, 0.5% SDS 25 mM EDTA and 0.1 mg/ml proteinase K) of the pelleted material overnight at 50° C. Nuclear DNA was extracted with phenol/chloroform twice followed by ethanol precipitation. PCR analysis was carried out as described above.

Cell Lines and Cytokine Genes

The murine transitional cell carcinoma cell line MB49 and cytokine genes were kindly provided by Dr. Timothy Ratliff at the University of Iowa. The cytokine genes were cloned into the pCI-neo expression vector (Promega). Plasmid DNA was prepared using Endofree plasmid Qiagen kits (Qiagen GmbH, Germany).

Animals

C57/BL6 female mice (approximately 4-6 weeks old) were obtained from the Laboratory Animals Centre of the National University of Singapore and maintained at the Animal Holding Unit of the university.

In Vitro Expression of Surface Markers $2×10^5$ cells were plated in 6 well tissue culture plates in RPMI 1640 supplemented with 10% FIBS (Biosciences, Australia), 2 mM L-glutamine, 50 U/ml penicillin and 0.05 mg/ml streptomycin (Sigma Chemical Company, St. Louis, Mo., USA). Cells were washed twice with 1×PBS and transfected with 7.5 µg of single cytokine genes and 3.75 µg of each cytokine gene for the IL-2+GMCSF combination, which was complexed with 20 µg of DOTAP (Roche Diagnostics, Mannheim, Germany) and 40 µg of methyl-β-cyclodextrin solubilized cholesterol (Sigma). The complexes were formed by making up the DNA and DMBC to 165 µl with 20 mM Hepes buffer (Gibco BRL, Rockville, Md., USA) and mixing for 15 min. This was made up to 1 ml with RPMI 1640 media, and added to wells for 2 h and then washed and replaced with 3 ml of fresh RPMI 1640 media. After 48 h, the cells were washed with PBS and fixed and labelled with anti-MHC I, anti-MHC II and anti-FAS, antibodies. The secondary antibody used was fluorescein isothiocynate (FITC; Pharmingen, Calif., USA). Isotype controls antibodies were also included. The labelled cells were analysed on a dual laser flow cytometer (Coulter Epics Elite, Florida, USA).

Antitumor Effects of Different Cytokine Treatments

A single cell suspension with $5×10^5$ viable MB49 cells in 0.1 ml of PBS was injected subcutaneously into the flank, 7 to 10 days before treatment. Only mice with a uniform tumor size of approximately 0.15-0.25 $cm^3$ were selected and randomized into groups for the intratumoral treatment. Treatments were carried out twice a week for three weeks by intratumoral injection and consisted of 100 µl of either 1×PBS, DMBC (Dotap+methylated-β-cyclodextrin containing cholesterol), IL-2+DMBC, GMCSF+DMBC, IFNγ+DMBC or the combination of IL-2+GMCSF+DMBC. Age matched tumor naive controls did not receive any treatment. Tumor size was measured with calipers every three days before injection up to day 38. The calculation for tumor volume was performed by the formula: length×width×height.

Single Cell Suspension and Flow Cytometry.

Spleens were harvested as described. Single cell suspensions were labelled with anti-CD4, αβ, γδ, NK and anti CD-8 antibodies that had been conjugated to phycoerithrin (PE) and CD3+ cells were labelled with antibodies conjugated to fluorescein isothiocynate (FITC). All antibodies were purchased from Pharmingen, Calif., USA. Labelled cells were analysed on a dual laser flow cytometer.

mRNA Extraction and RT-PCR

For total RNA extraction, spleen were homogenized in 1 ml of Trizol reagent (Gibco BRL, Rockville, Md., USA) according to the manufacturers instructions. RT-PCR was carried out as described.

EXAMPLES

Example 1

In Vitro Transfection Efficiency of Non-Viral Agents

The pCMVlacZ expression plasmid was used to assess the transfection efficiency of various non-viral agents, in a 2 hour time period, on MB49 cells. Both DOTAP and Superfect were able to transfect MB49 cells within a 2 h time period with efficiencies of approximately 20.4% and 14.8% respectively (see Table 1 below).

TABLE 1

| Non-viral agent | Type | Transfection efficiency |
| --- | --- | --- |
| DOTAP | Cationic Lipid | 20.4% |
| Superfect | Dendrimer | 14.8% |
| Fugene | Non-liposomal | 1.02% |
| Calcium chloride | Chemical | 0% |
| DEAE-Dextran | Chemical | 0% |

Transfection conditions were optimized for each agent, to ensure maximum transfection at 2 h. Transfection efficiency was measured by counting the percentage of cells stained blue with X-gal. Optimal transfection was obtained using 7.5 µg of DNA and 20 µg DOTAP. With Superfect, a much lower amount of DNA was needed to obtain similar transfection rates as DOTAP namely 2 µg DNA with 7.5 µl of Superfect. A very low transfection rate of 1.02% was obtained with Fugene. Neither calcium chloride (0-40 µg) nor DEAE-Dextran (0-2 µg) nor naked DNA could transfect MB49 cells.

Figure 1E:
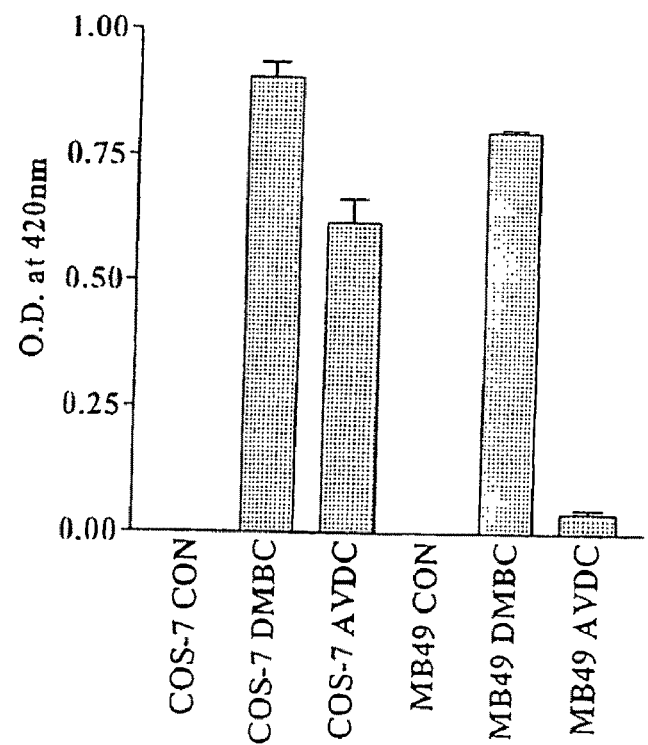
FIG. 1E is a bar graph showing a comparison of the transfection efficiency of DMBC and conventional DOTAP:cholesterol (AVDC). Untransfected cells (CON) showed no β-gal activity as measured by the optical density at 420 nm. AVDC was able to transfect Cos-7 cells but did not transfect MB49 cells efficiently. In contrast DMBC was able to transfect MB49 cells and enhance transfection efficiency in Cos-7 cells.

To improve transfection rates, MBC was mixed with DOTAP immediately prior to the addition of DNA and the mixture incubated for 15 min at room temperature. Addition of MBC resulted in an increase in the number of cells that were successfully transfected as shown in FIG. 1A-C. The increase in transfection efficiency was 3.9 fold when MBC was used in combination with DOTAP and 2.4 fold with Superfect (FIG. 1D). However, the amount of MBC needed to produce this increase in transfection efficiency varied with the agent used. Optimal DOTAP transfection was obtained with 40 µg of MBC while 10 µg was optimal for Superfect. As the best transfection rates were obtained with DOTAP+MBC (DMBC), this combination was used in all further experiments. A comparison was also made between the transfection efficiency of DMBC and a conventional DOTAP:cholesterol (1:1) mixture (AVDC). AVDC was able to transfect Cos-7 cells but did not transfect MB49 cells very well. In contrast, DMBC was able to transfect MB49 cells as well as enhance the transfection of Cos-7 cells when compared to AVDC (FIG. 1E).

Example 2

Duration of β-Galactosidase Gene Expression

Figure 2A:
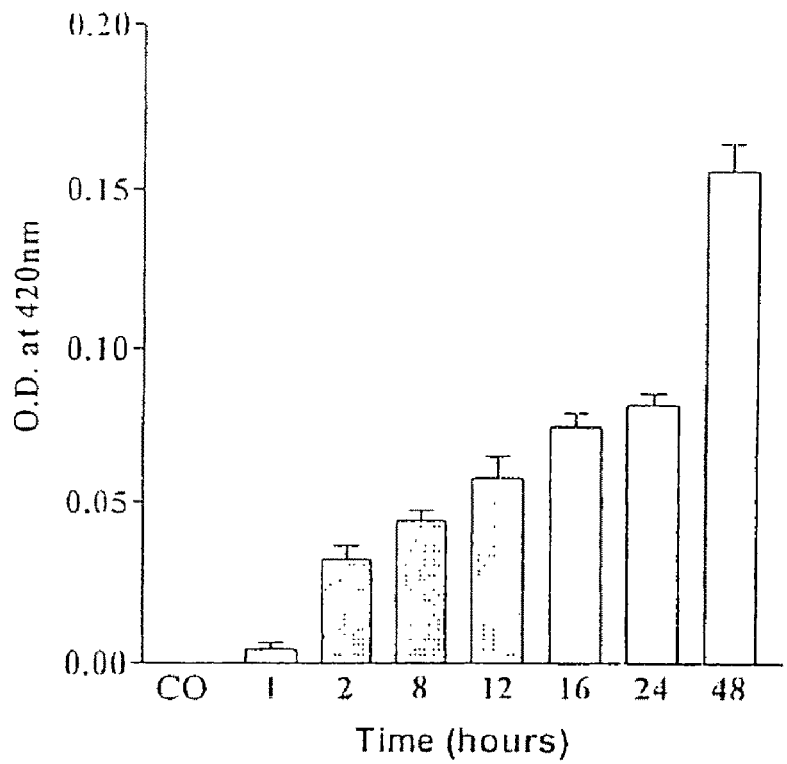
FIGS. 2A-2B are bar graphs showing expression of the pCMVLacZ gene with time. β-gal activity was seen as early as one hour after transfection and steadily increased up to 48 h (FIG. 2A). Cells were transfected as described in the Examples section and assayed for β-gal activity using the ONPG assay after 2, 4, 6, 8 and 12 days. β-gal expression was much lower at 12 days (FIG. 2B).
Figure 2B:
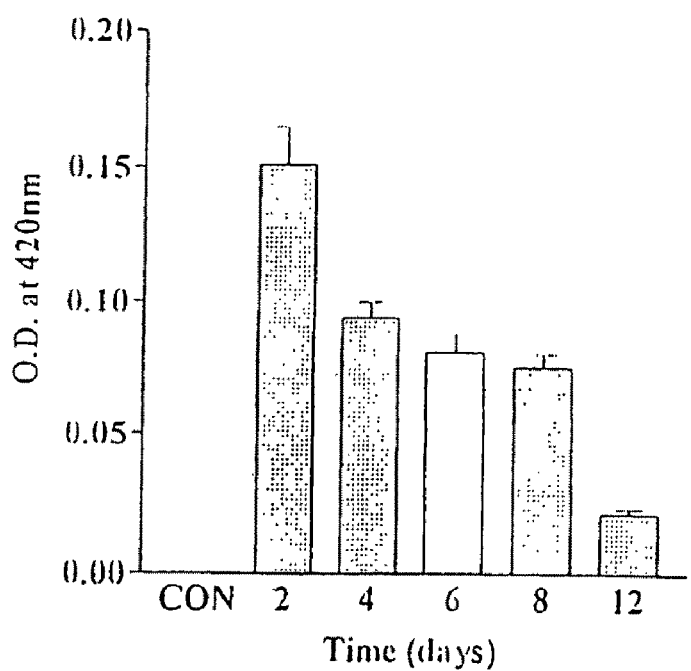

Characterization of β-galactosidase (β-gal) gene expression as a function of time following transfection with DMBC was done. As shown in FIG. 2A, protein expression, as determined by the ONPG assay, occurred within 1 h of the removal of the agent and increased up to 48 h post transfection. After 48 h, there was a steady decrease in protein expression and by 12 days post-transfection, the β-gal activity had decreased by 7 fold compared to the expression at day 2 (FIG. 2B). It appears that as the cells replicate, the gene is lost and/or silenced.

Example 3

DNA Uptake Following Transfection

Figure 3A:
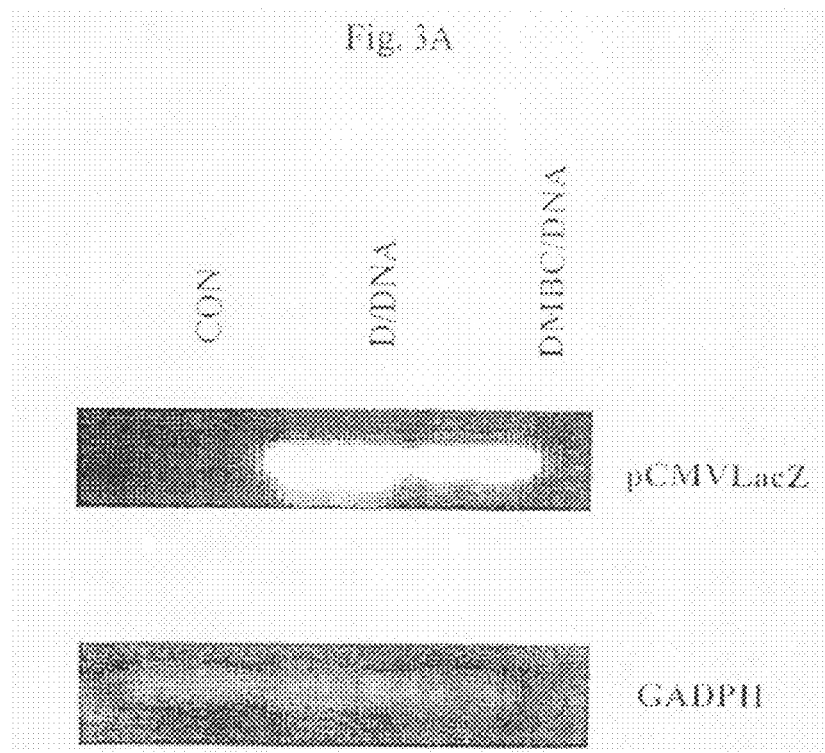
FIGS. 3A-3B demonstrate DNA internalization by cells exposed to either DOTAP (D) or DMBC. The presence of the LacZ gene was determined for untransfected and transfected cells using PCR (FIG. 3A). GADPH was used as a positive control. The expression of the LacZ gene relative to GAPDH was determined by densitometric scanning of the PCR products after agarose gel electrophoresis (FIG. 3B).
Figure 3B:
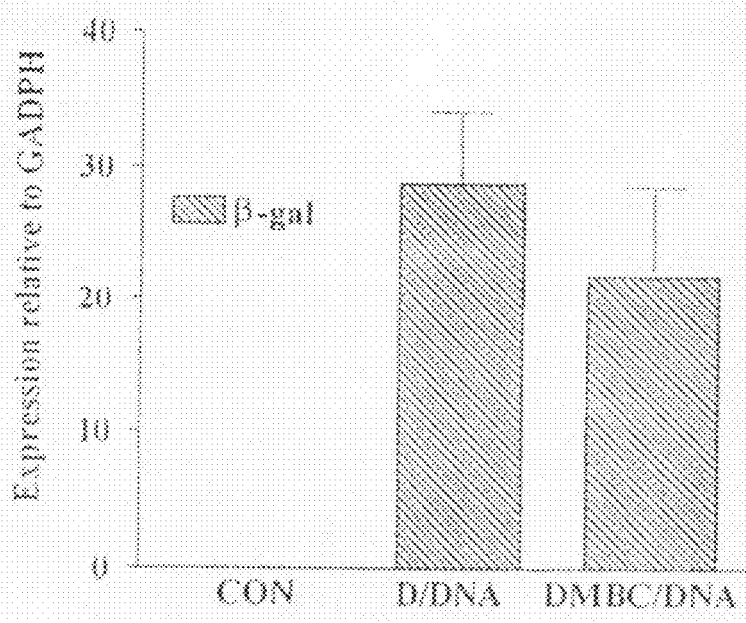

In order to determine whether there was a difference in DNA uptake when using DOTAP and DMBC, the quantity of plasmid DNA extracted from cells was measured 2 h after transfection. To minimize the amount of surface bound DNA and get a better estimate of true DNA uptake; multiple washes were performed with 1×PBS as well as digestion with DNAse. FIGS. 3A and 3B show the PCR analysis of DNA extracted from MB49 cells. MB49 cells seem to have internalized similar amounts of plasmid DNA with both agents. Therefore, the differences observed in transfection efficiencies are not due to the differential uptake of plasmid DNA but perhaps to the stability of the DNA once taken into cells.

Example 4

Nuclear and Cytoplasmic Accumulation of Plasmid DNA

Figure 4A:
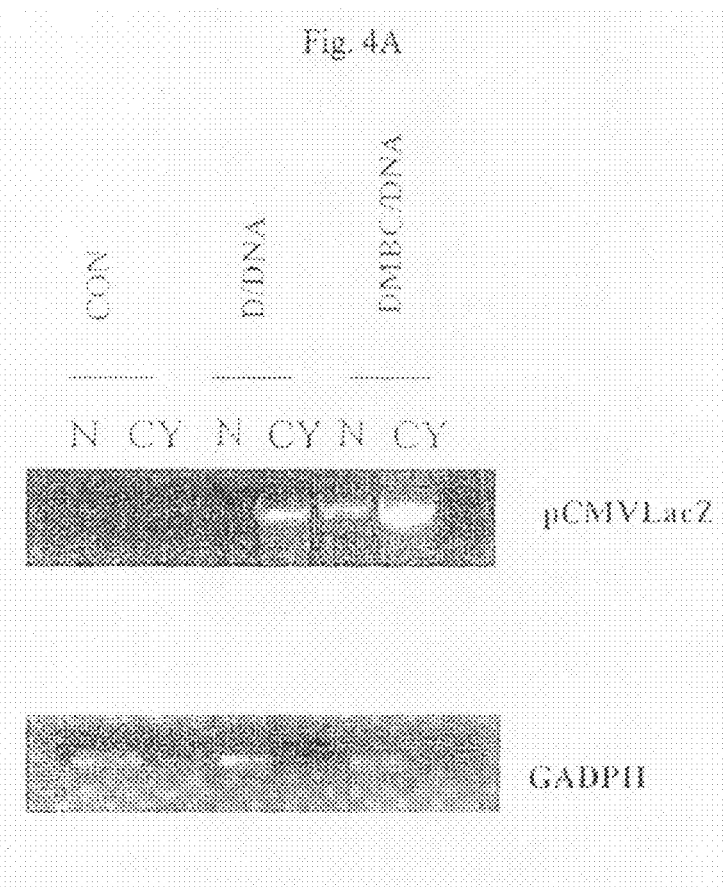
FIGS. 4A-4B demonstrate localisation of plasmid DNA by PCR.
Figure 4B:
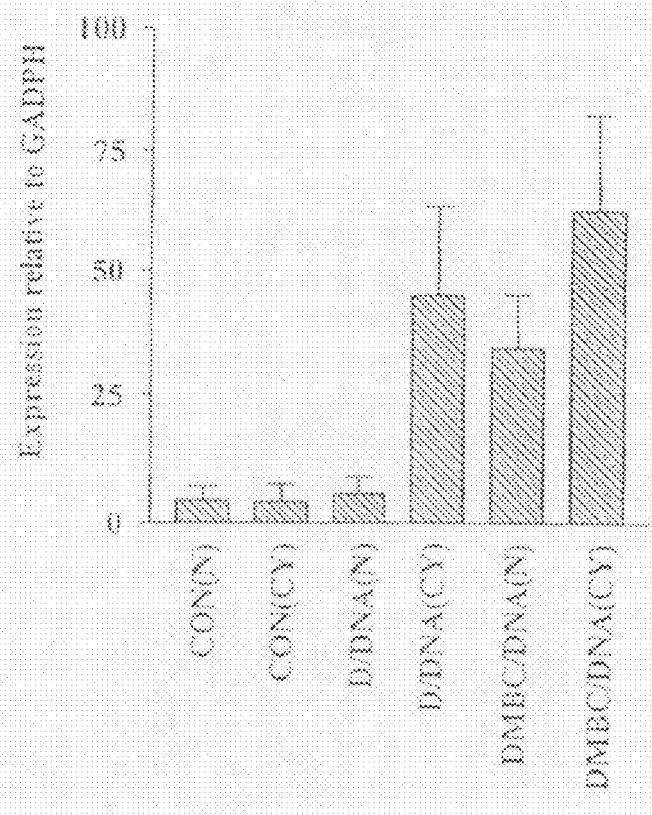

To determine the localization of DNA following transfection with DOTAP and DMBC, nuclear and cytoplasmic extracts were prepared from transfected cells. The presence of DNA in these extracts was determined using PCR. In cells transfected with DMBC, the LacZ gene was located in both the nucleus and the cytoplasmic fractions. However with DOTAP alone, the plasmid DNA was only found to be in the cytoplasm (FIGS. 4A and 4B). The GADPH gene was used to confirm the presence of nuclear DNA in nuclear extracts and the lack of contamination of cytoplasmic fractions with nuclear DNA.

Example 5

Toxicity of DMBC/DNA Complexes

Figure 5A:
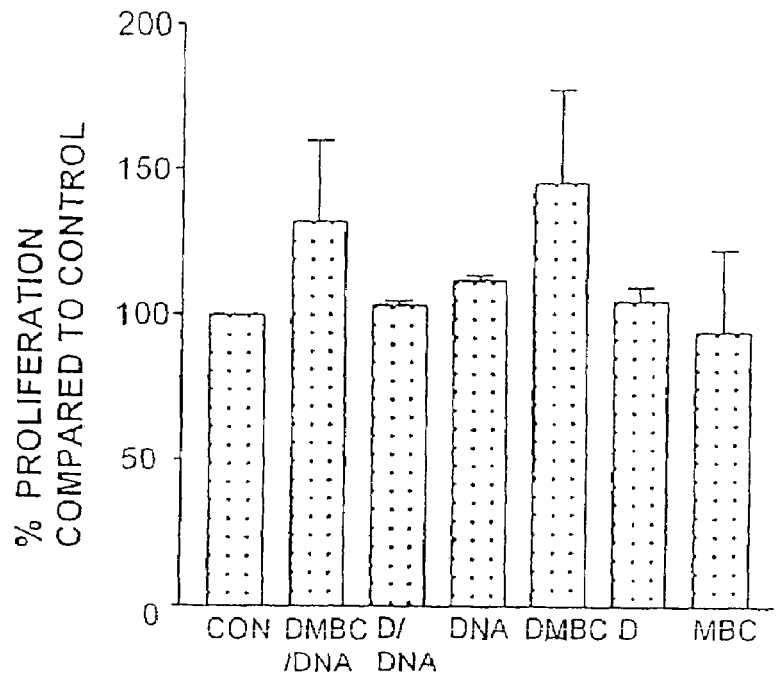
FIGS. 5A-5B are bar graphs showing antiproliferative effect of the DNA:DMBC complex. The antiproliferative effect of the following agents; DM BC/DNA, DOTAP(D)/DNA, DNA, DMBC, DOTAP(D) and MBC were compared to untreated MB49 cells (CON) after a 2 h (FIG. 5A) and 24 h (FIG. 5B) exposure. The relative antiproliferative effect was determined 48 h later by comparing the incorporation of [$^{14}$C]-thymidine in transfected and untransfected cells.
Figure 5B:
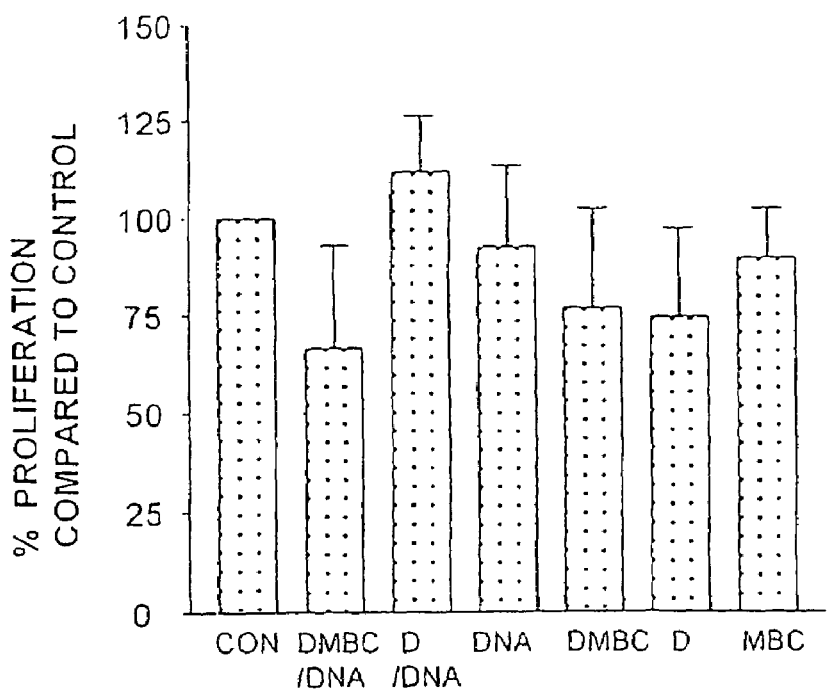

A cell proliferation assay was used to gauge the toxicity of the transfection agents. Relative toxicity was measured by comparing proliferation in transfected and untransfected cells, 48 h after plating. Cells were exposed to the transfection agents for 2 h and 24 h. There was no difference in the level of $^{14}$C-thymidine incorporation between transfected and untransfected cells exposed to either DOTAP (D) or DMBC for 2 h (FIG. 5A). When cells were exposed to DMBC with or without DNA or to DOTAP for 24 h, there was a reduction in cell proliferative capacity but this was not statistically significant (FIG. 5B).

Example 6

Figure 6A:
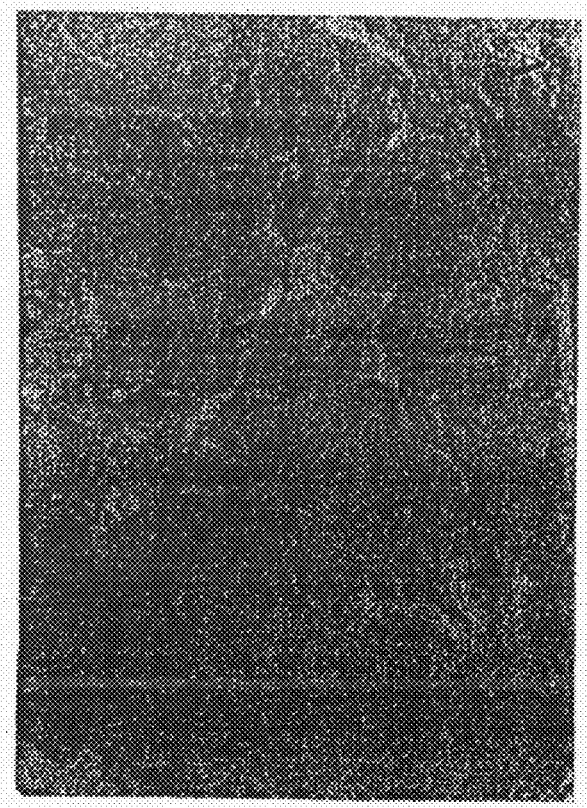
FIGS. 6A-6B are photographs showing transfection of urothelial cells in vivo. Transfected bladders were harvested 2 days later and stained for β-galactosidase activity. The untransfected bladder was used as a negative control (FIG. 6A). In the transfected bladder, epithelial cells facing the lumen stained positive (FIG. 6B). (Magnification ×40)
Figure 6B:
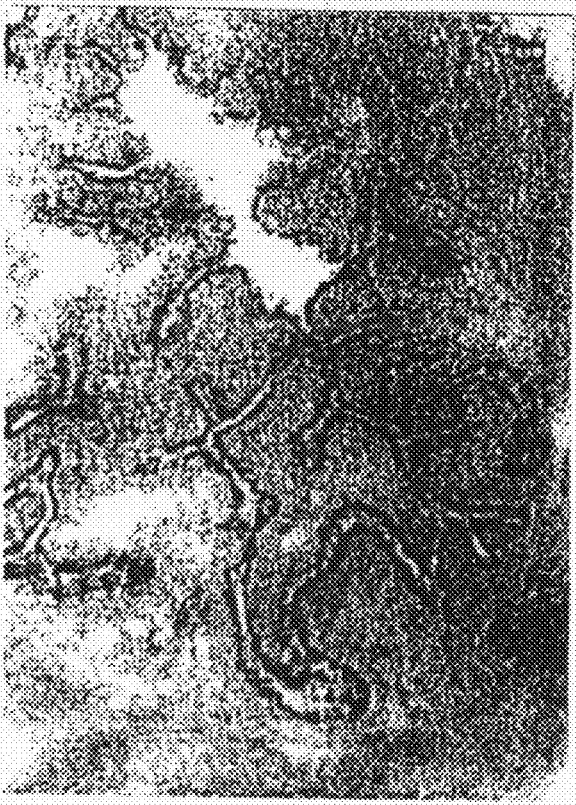

Transfection of Murine Bladders by Intravesical Instillation of the Transfection Agent and DNA In mice (n=16) that received the transfection agents DMBC/DNA via an intravesical instillation, bladder epithelial cells facing the lumen were successfully transfected (FIGS. 6A and 6B) in all mice. In vivo DOTAP alone did not result in efficient transfection of bladder epithelial cells. As well as the bladder, the lungs, kidneys, spleen, heart and liver were also harvested from transfected animals and controls and were all found to stain negative for β-gal, showing that transfection was limited to the bladder, as summarized in Table 2 below:

TABLE 2

Staining with pCMVLacZ
Table 2. Staining limited to bladder

| Organs | β-gal activity |
| --- | --- |
| Bladder | Positive |
| Lungs | Negative |
| Liver | Negative |
| Heart | Negative |
| Kidney | Negative |
| Spleen | Negative |

This was confirmed by PCR analysis (FIG. 7) performed on two mice. In mice, spleen cells were harvested at the same time as the bladders and the levels of CD3+, CD4+, CD8+, αβ and γδ T cells in control and transfected animals determined by flow cytometry. No difference was found between the control and experimental groups.

Figure 10A:
FIGS. 10A-10B are photographs showing X-gal staining of normal (FIG. 10A) and hyperplasia (FIG. 10B) bladder sections. Bladder implanted with MB49 tumor cells were transfected with pCMVlacZ:DMBC for 2 h. Blue staining was observed in the superficial luminal cell layers of the hyperplasia. (Magnification ×100).
Figure 10B:
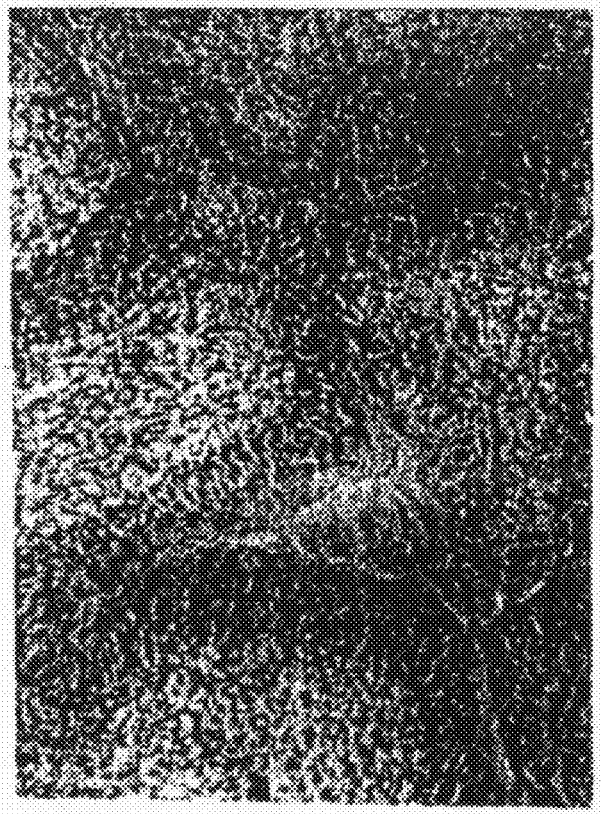

Additionally, tumors were implanted in mice bladders and once established these mice were also treated intravesically with pCMVlacZ and DMBC. The superficial luminal cell layers of the hyperplasia showed β-gal staining (FIG. 10A-10B).

The effect of DMBC and DOTAP on transfected bladders were analysed by transmission electron microscopy. The analyses indicated that the 2 h transfection exposure time with either agent did not result in any discernible structural difference in the cells facing the lumen when compared with an untransfected control bladder. There was also no indication of the accumulation of cationic lipids or cholesterol in vacuoles. Bladder epithelial cells generally contain many vacuoles but there did not appear to be an increase in the number of such vacuoles after treatment.

Example 7

Figure 8A:
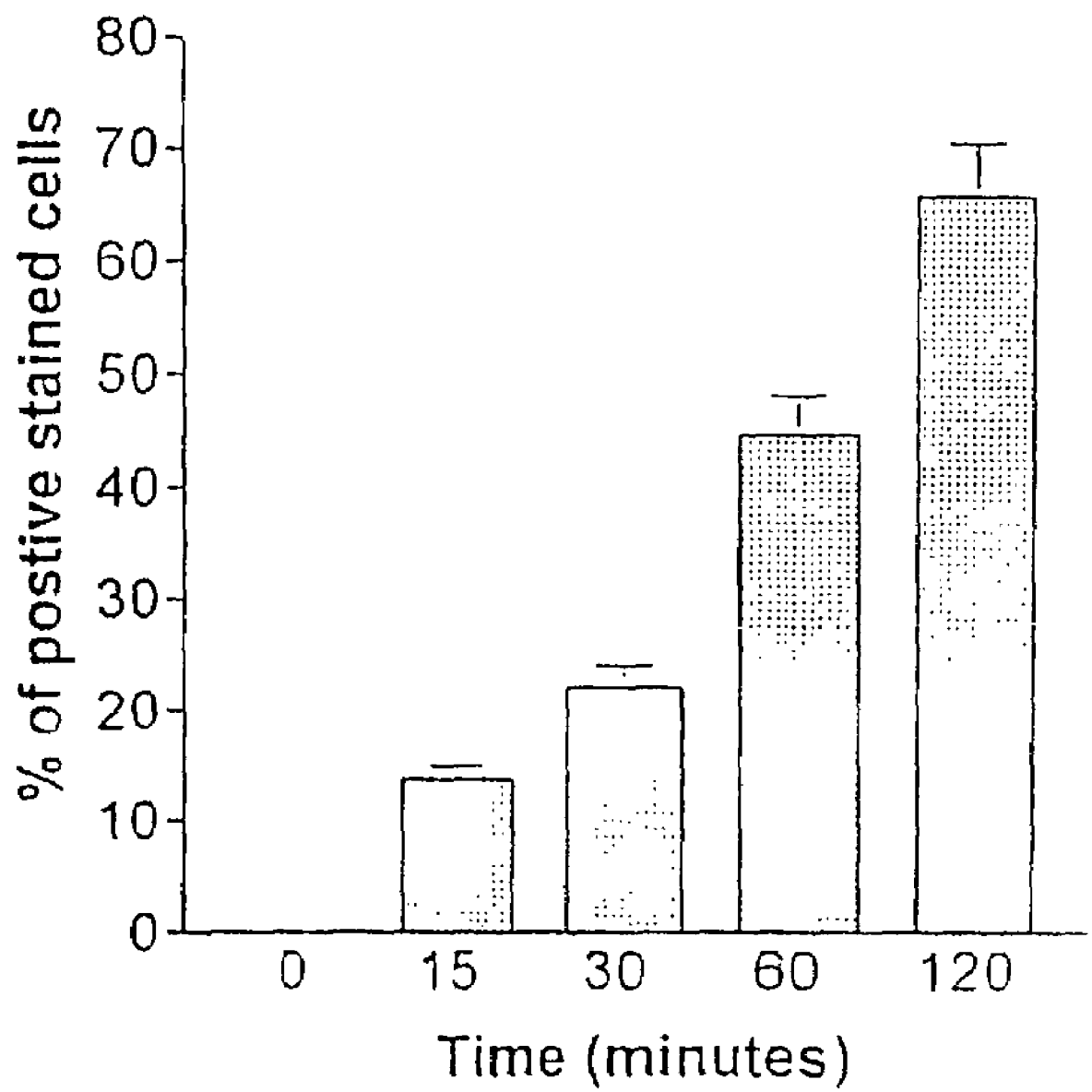
FIG. 8A is a bar graph showing the effect of exposure times on transfection efficiency in vitro. Cells were exposed to the DNA:DMBC complex for 15, 30, 60 and 120 min in vitro. Longer exposure times improved the transfection efficiency as measured by the percentage of cells stained positive with X-gal.

Efficiency of Transfection with Respect to Time of Exposure to Transfection Agents In order to determine the transfection efficiency with shorter exposure times, the transfection complex (pCMVlacZ:DMBC) was applied to the cells for different time periods, following which it was removed and the cells cultured in complete medium for 48 h before harvesting and enzymatic analyses. β-Gal activity is detectable even when the transfection time is as short as 15 min and this activity increases with the duration of exposure to the transfection agent (FIG. 8A). There is a 4.8 fold difference in transfection rates between a 15 min exposure and a 2 h exposure. In vivo, with longer exposure times more of the epithelial cells facing the lumen were transfected (FIG. 8B).

Example 8

Duration of Gene Expression In Vivo

Figure 9A:
FIGS. 9A-9B are photographs showing the duration of expression in vivo after a single intravesical instillation. Two days after transfection the majority of cells facing the lumen stained positive with X-gal (FIG. 9A). Thirty days later β-gal expression could still be observed in a reduced number of cells (FIG. 9B) (Magnification ×100).
Figure 9B:
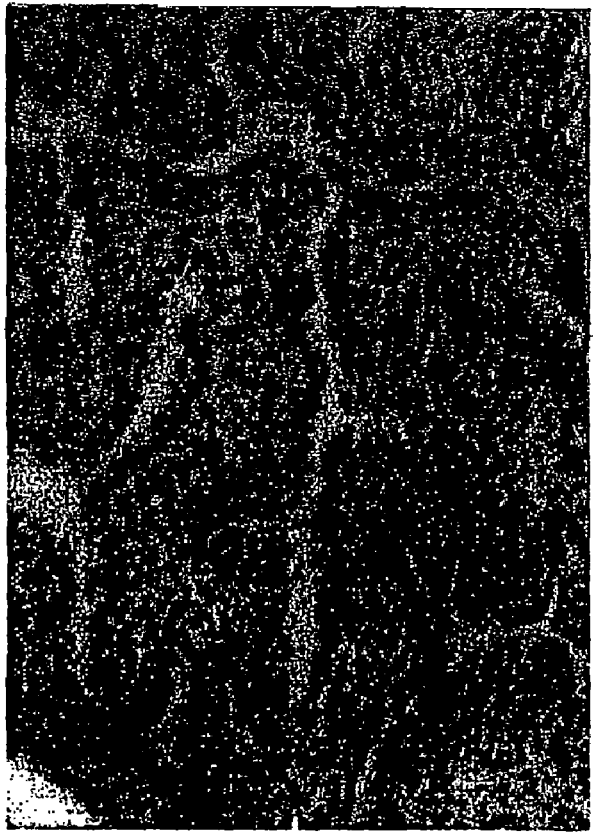

In mice β-gal expression was monitored at 14, 21 and 30 days post transfection. By 30 days, expression was greatly reduced but still clearly detectable (FIGS. 9A and 9B). The durability of the signal could be the result of a low turnover of urothelial cells in vivo which would result in the presence of the pCMVlacZ gene for a longer time.

Example 9

Characterization of the Effects of DOTAP+methylated-β-cyclodextrin Solubilized Cholesterol (DMBC) and Transfected Cytokine Genes on MB49 Cells and Tumor Growth In Vitro Expression of Surface Protein Markers MB49 cells were transfected with cytokine genes singly and in combination. Two days later expression was determined by flow cytometry. An increase in the proportion of cells that expressed MHC class I, MHC class II, FAS, ICAM I, ICAM II, B71 and B72 was seen in cells transfected with the cytokines gene when compared to untransfected cells, as summarized in Table 3, below.

TABLE 3

In vitro expression of surface protein markers.

| SAMPLE | MHC I | MHC II | FAS | B7-1 | B7-2 | ICAM I | ICAM II |
|---|---|---|---|---|---|---|---|
| UNTREATED | 11.1 | 14.0 | 13.2 | 14.6 | 11.8 | 13.7 | 15.1 |
| IL-2 | 29.8 | 19.7 | 68.5 | 73.4 | 44.5 | 27.49 | 73.8 |
| GMCSF | 45.2 | 17.4 | 67.1 | 54.3 | 28.9 | 58.6 | 75.8 |
| IL-2 + GMCSF | 65.6 | 37.7 | 76.9 | 73.2 | 73 | 70.1 | 67.9 |
| IFN-γ | 47.87 | 25.2 | 74.4 | 70.7 | 35.8 | 30.4 | 67.8 |
| DMBC | 29.5 | 25.4 | 34 | 52.7 | 31.4 | 27.3 | 46.1 |
| PCINEO | 24.3 | 15.8 | 24.3 | 31 | 26.3 | 19.3 | 26.3 |

Intratumoral Therapy of Established Tumors

Figure 11:
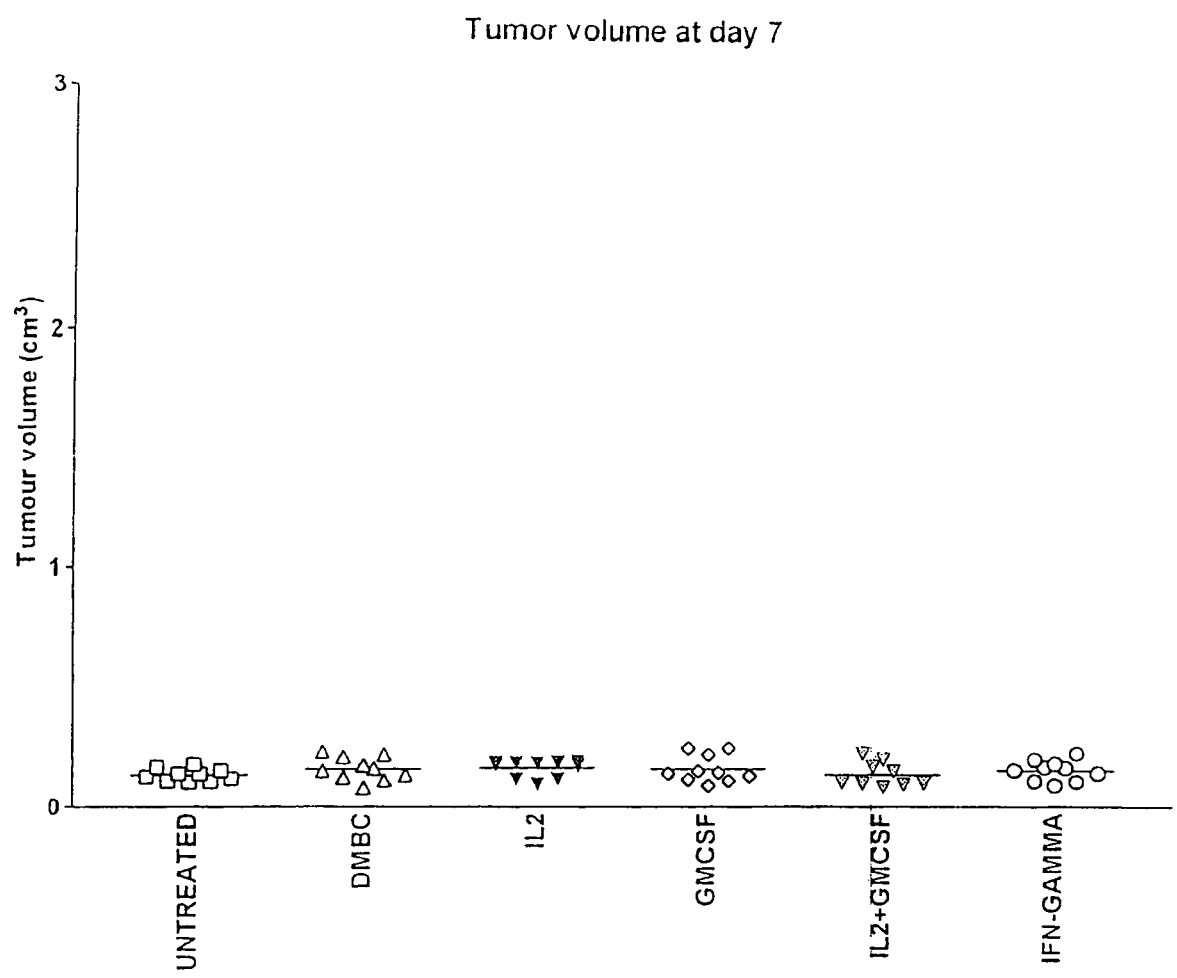
FIG. 11 is a graph showing tumor volume at day 7 in mice treated with cytokine gene therapy (IL-2, GMCSF, IL-2+ GMCSF or IFN-γ), or with DMBC or in an untreated control.
Figure 12:
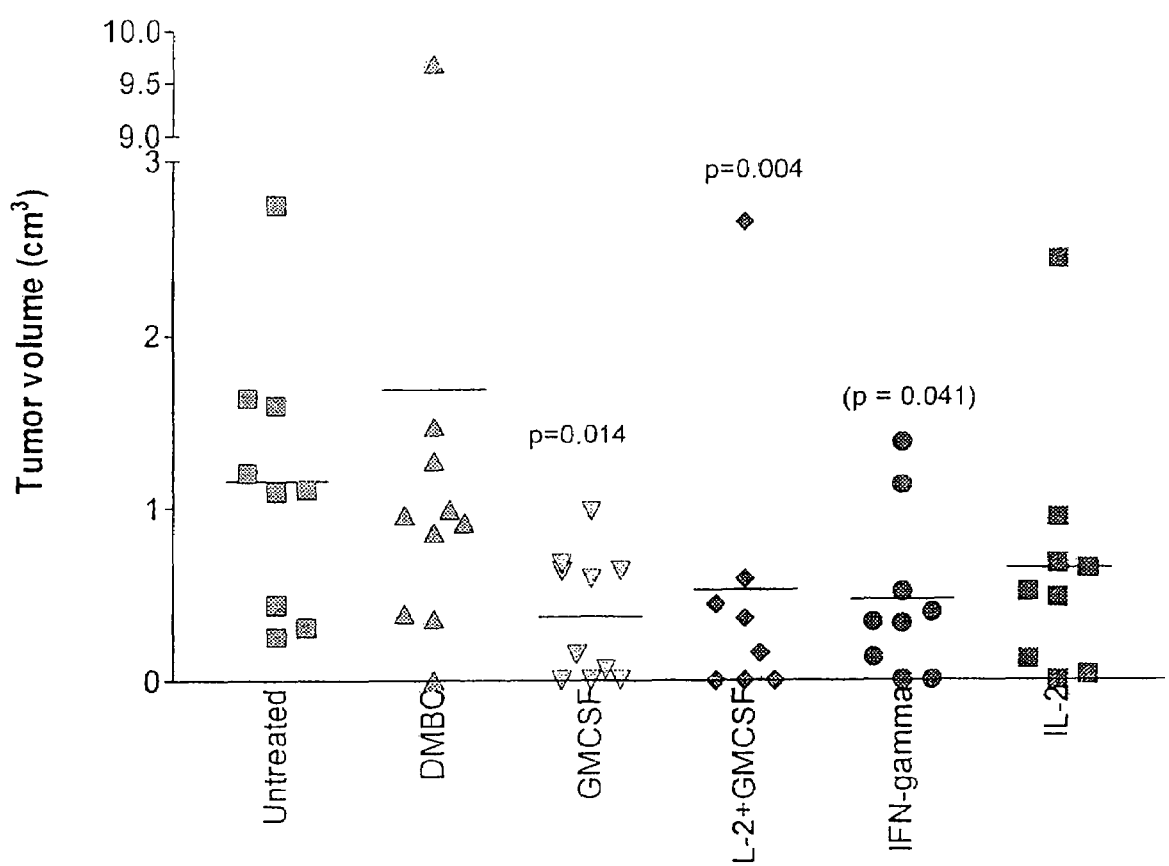
FIG. 12 is a graph showing tumor volume at day 38 in mice treated with cytokine gene therapy (IL-2, GMCSF, IL-2+ GMCSF or IFN-γ), or with DMBC or in an untreated control.
Figure 13:
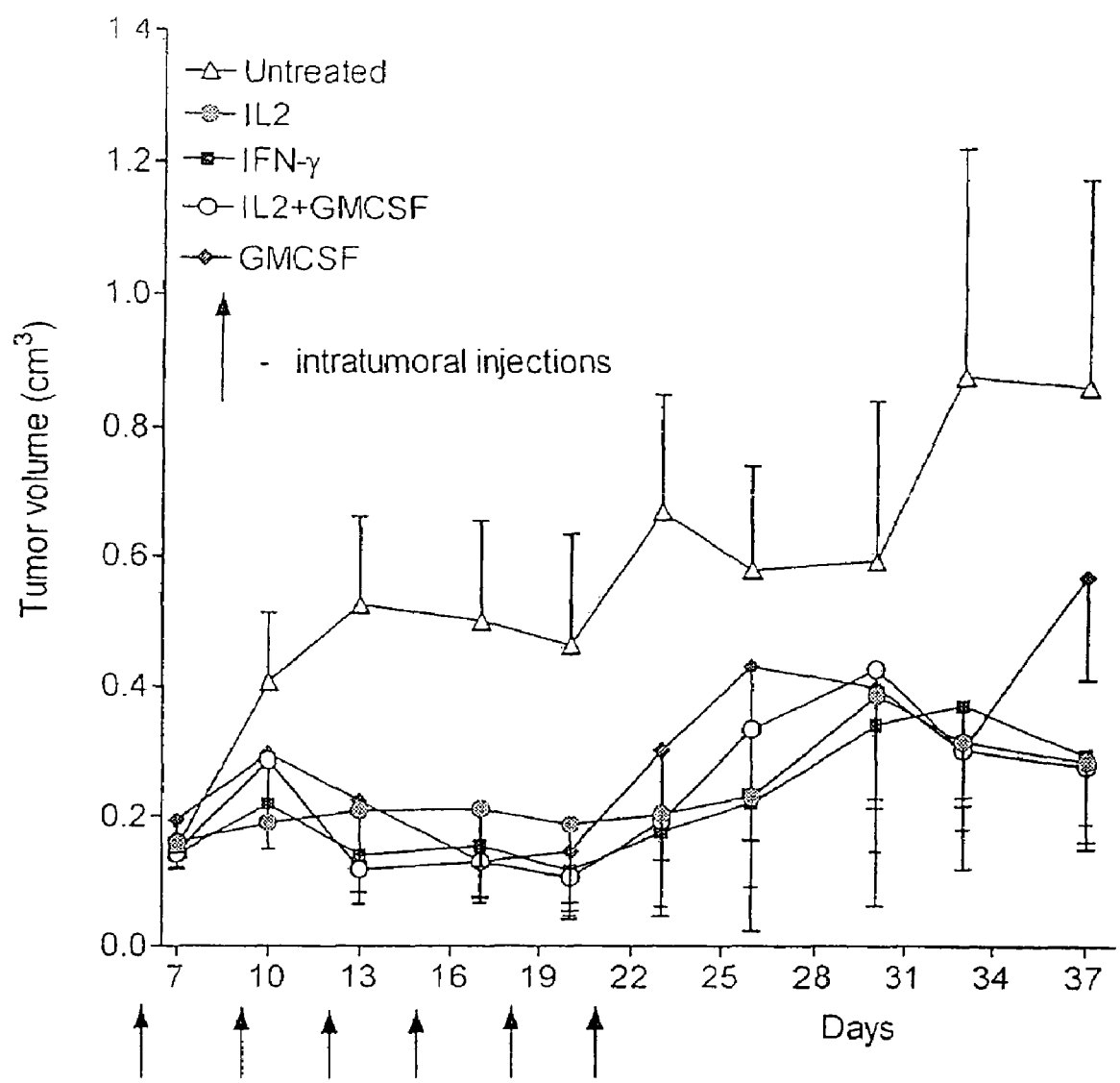
FIG. 13 is a graph showing tumor volume over time (days 7-37) in mice treated with cytokine gene therapy (IL-2, GMCSF, IL-2+GMCSF or IFN-γ), or with DMBC or in an untreated control.

The ability of the transfection system of the invention to deliver cytokines for the eradication of established tumors was tested. The transfection compositions comprising DNA encoding the following cytokines (IL-2, IFN-γ, GMCSF and IL-2+GMCSF) were injected intratumorally in the right flank of tumor-bearing mice 7-10 days after tumor implantation. The tumor volume in the mice at day 7 is shown in the graph of FIG. 11. Mice treated with cytokine gene therapy demonstrated slower tumor group compared to the untreated and DMBC controls. Tumor volume at day 38 (shown in the graph of FIG. 12) was significantly smaller for mice transfected with either IFN-γ ($p=0.041$), GMCSF ($p=0.0014$) or IL-2+GMCSF ($p=0.004$). Mice treated with IL-2 only demonstrated slower tumor growth. Thirty percent of all mice treated with IFN-γ, GMCSF and IL-2+GMCSF were cured. Tumor volume over the time (days 7-37) is summarized in the graph of FIG. 13. In the untreated group one mouse showed local remission but rapidly lost weight and died prematurely suggesting metastatic disease. The cure rate in the mice is summarized in Table 4 below:

TABLE 4

Cure Rate

| Treatment | Complete Local Remission |
|---|---|
| UNTREATED | 1/10 |
| DMBC | 1/10 |
| IL-2 | 1/10 |
| IFN-γ | 3/10 |
| GMCSF | 3/10 |
| GMCSF + IL-2 | 3/9 |

Cytokine Expression in Splenocytes

Cytokine expression in the splenocytes of untreated and cytokine treated tumor bearing mice was compared with those of normal (no tumor) mice to see if cytokine production was affected. All groups expressed mRNAs for IL-2, IFN-γ, TNF-α and GMCSF. Cytokine treated mice showed a general increase in cytokine mRNA production from splenocytes compared to the untreated, DMBC and normal (no tumor) controls. Mice treated with GMCSF and IL-2+GMCSF produced the largest amounts of GMCSF compared to the other cytokine treated groups. The results are summarized below in Table 5:

TABLE 5

| Treatment groups | mRNA levels relative to GAPDH (fold increase) | | | |
|---|---|---|---|---|
| | IL-2 | IFN-γ | GMCSF | TNF-α |
| IL-2 | 8.4 | 3.21 | 14.5 | 7.3 |
| GMCSF | 5.6 | 2.92 | 22.6 | 5.25 |
| IFN-γ | 2.3 | 6.4 | 10.4 | 7.8 |
| IL-2 + GMCSF | 1.5 | 6.2 | 28 | 7.3 |
| PARENTAL | 1 | 1 | 1 | 1 |
| CONTROLS | 0.19 | 1.5 | 1.2 | 0.6 |
| DMBC | 0.18 | 0.6 | 1.4 | 5.5 |
| IL-2 + GMCSF + IFN-γ | 4.3 | 1.9 | 8.8 | 8.9 |
| IL-2 + IFN-γ | 1.7 | 1.8 | 0.97 | 0.9 |

Phenotypic Characterization of Splenocytes

Flowcytometric analysis of splenocytes from mice with phenotype-specific monoclonal antibodies showed that the CD3, CD4+ and CD8 populations in the untreated and DMBC treated groups were decreased when compared to normal controls. Tumor bearing mice treated with cytokine gene therapy had similar profiles to normal controls for CD3, CD4+, CD8, NK and αβ populations. The results are summarized below in Table 6:

TABLE 6

| Treatment | CD4% | CD8% | CD3% | αβ % | γδ % | NK |
|---|---|---|---|---|---|---|
| UNTREATED | 11.89 ± 1.09 | 5.32 ± 0.49 | 12.71 ± 1.11 | 66.13 ± 5.59 | 3.04 ± 0.55 | 75 ± 12 |
| DMBC | 10.59 ± 0.92 | 6.34 ± 0.74 | 17.12 ± 1.60 | 53.68 ± 4.9 | 31.61 ± 7.6 | 28.58 ± 1.919 |
| CONTROL | 16.81 ± 0.94 | 11.7 ± 0.60 | 27.38 ± 1.11 | 74.15 ± 4.59 | 2.45 ± 0.32 | 31.2 ± 5.03 |
| IL-2 | 14 ± 1.16 | 16.65 ± 1.61 | 23.97 ± 2.1 | 53 ± 4.57 | 2.84 ± 0.497 | 26.68 ± 2.53 |
| GMCSF | 17.92 ± 1.74 | 17.41 ± 1.73 | 22.42 ± 2.3 | 47.18 ± 3.5 | 3.11 ± 0.46 | 29.02 ± 4.52 |
| IL-2 + GMCSF | 22.9 ± 2.46 | 14.47 ± 1.34 | 31.13 ± 4.2 | 49.33 ± 2.56 | 12.65 ± 2.72 | 64.42 ± 14.41 |
| IFN-γ | 21.50 ± 1.94 | 15.66 ± 1.77 | 22.54 ± 2.62 | 37.86 ± 3.08 | 2.48 ± 0.4753 | 22.86 ± 2.56 |

The results described in this example demonstrate that transfection of murine bladder cancer cells with single cytokine genes induces an increase in MHC class I, class II and Fas expression. This response could make the cancer cells more immunogenic. From the intratumoral transfection experiment, it was found that IL-2, IFN-γ, GMCSF and II-2+GMCSF had similar inhibitory effects on tumor growth. After 37 days, it was found that there was a significant difference in tumor size in the groups transfected with IFN-γ, GMCSF, IL-2+GMCSF when compared to the untreated group. This data demonstrates that DMBC is an effective agent for the transfection of urothelial cells in vitro and in vivo. The intratumoral studies in mice indicate that the transfection of urothelial tumor cells with cytokine gene delivery by non-viral vectors can result in the abrogation of tumor growth.

Although the foregoing invention has been described in some detail by way of illustration and example for purposes of clarity and understanding, it will be apparent to those skilled in the art that certain changes and modifications may be practical. Therefore, the description and examples should not be construed as limiting the scope of the invention, which is delineated by the appended claims.

The invention claimed is:

1. A method of treating bladder cancer in a subject, the method comprising:
   delivering a transfection composition intravascularly into the bladder of a subject, such that bladder cancer cells of the subject are transfected with the polynucleotide, wherein the polynucleotide imparts anti-cancer activity against bladder cancer cells, wherein the transfection composition comprises:
   (i) a polynucleotide;
   (ii) a cationic lipid, a cationic polymer or a dendrimer, or combinations thereof; and
   (iii) a solubilized cholesterol preparation, wherein the solubilized cholesterol preparation comprises cholesterol solubilized with a cyclodextrin.

2. The method of claim 1, wherein the cyclodextrin is methyl-β-cyclodextrin.

3. The method of claim 1, wherein the cyclodextrin is selected from the group consisting of alpha-cyclodextrin, beta-cyclodextrin, gamma-cyclodextrin, sulfated beta-cyclodextrin, tertiary amine beta-cyclodextrin, quaternary amine beta-cyclodextrin, 2-hydroxypropyl-beta-cyclodextrin, 2,6-di-O-methyl-beta-cyclodextrin, hydroxyethyl-beta-cyclodextrin, 6-deoxy-6-S-beta-D-galactopyranosyl-6-thio-cyclomalto-heptaose, sulfobutylether-beta-cyclodextrin, carboxymethyl-beta-cyclodextrin, carboxymethyl-ethyl-beta-cyclodextrin, diethyl-beta-cyclodextrin, dimethyl-beta-cyclodextrin, random methyl-beta-cyclodextrin, glucosyl-beta-cyclodextrin and maltosyl-beta-cyclodextrin.

4. The method of claim 1, wherein (ii) is a cationic lipid which is 1,2-diacyl-3-trimethylammonium propane (DOTAP).

5. The method of claim 1, wherein (ii) is a dendrimer which is a cationic dendrimer.

6. The method of claim 1, wherein the cationic lipid, cationic polymer or dendrimer is selected from the group consisting of dioleoyl phosphatidylethanolamine (DOPE), [2,3-bis(oleoyl)propyl]trimethyl ammonium chloride (DOTMA), dioctadecyl amido glycyl spermine (DOGS), dioctadecyl diammonium bromide (DODAB), dioctadecyl diammonium chloride (DODAC), 2,3dioleoyloxy-N-[sperminecarboxami-noethyl]-N—N-dimethyl-1-propanamimium (DOSPA), 3β[N-n',N'-dimethylaminoethane)-carbamoyl]cholesterol, dioleoyl (DC-Chol), (1-[2-oleoyloxy-ethyl]-2-oleo yl-3-(2-hydroxyethyl) imidazolinium chloride (DOIC), dioleoyl phosphatidylcholine (DOPC), dimyristooxypropyl dimethyl hydroxyethyl ammonium bromide (DMRIE), polyaminodoamine (PAMAM), polylysine, polyhistidine, polyarginine, polyethyleneimine, poly(4-vinylpyridine), poly(vinylamine), poly(4-vinyl-N-alkyl pyridinium halide), or combinations thereof.

7. The method of claim 1, wherein the polynucleotide comprises at least one expression vector encoding at least one protein selected from the group consisting of interleukins, interferons, colony stimulating factors, anti-angiogenic factors, anti-metastatic factors, membrane receptors and tumor suppressors.

8. The method of claim 1, wherein the polynucleotide comprises an expression vector encoding a protein selected from the group consisting of interleukin-1 (IL-1), interleukin-2 (IL-2), interleukin-12 (IL-12), interleukin-13 (IL-13), interleukin-18 (IL-18), interferon-α, interferon-β, interferon-γ, granulocyte-macrophage colony stimulating factor (GMCSF), granulocyte colony stimulating factor (GCSF), p53, and an antagonist of vascular endothelial cell growth factor (VEGF).

9. The method of claim 1, wherein the polynucleotide comprises an expression vector encoding interleukin-2 (IL-2).

10. The method of claim 1, wherein the polynucleotide comprises an expression vector encoding granulocyte macrophage colony stimulating factor (GMCSF).

11. The method of claim 1, wherein the polynucleotide comprises an expression vector encoding interferon-γ.

12. The method of claim 1, wherein the polynucleotide comprises at least one expression vector encoding two or more of interleukin-2 (IL-2), granulocyte macrophage colony stimulating factor (GMCSF) and interferon-γ.

13. The method of claim 1, which further comprises performing an additional anti-bladder cancer treatment on the subject.

14. The method of claim 13, wherein the additional anti-bladder cancer treatment comprises Bacillus Calmette-Guerin (BCG) therapy.

* * * * *